US008318912B2

(12) United States Patent
Simon

(10) Patent No.: US 8,318,912 B2
(45) Date of Patent: Nov. 27, 2012

(54) TARGETED IMMUNE CONJUGATE COMPRISING AN ANTIBODY TO GLYCOPHORIN A AND A M2E PEPTIDE

(75) Inventor: Paul M. Simon, Wilmington, DE (US)

(73) Assignee: Augmenta Biologicals, LLC, Wilmington, DE (US)

( * ) Notice: Subject to any disclaimer, the term of this patent is extended or adjusted under 35 U.S.C. 154(b) by 565 days.

(21) Appl. No.: 12/306,457

(22) PCT Filed: Jun. 22, 2007

(86) PCT No.: PCT/US2007/071875
§ 371 (c)(1),
(2), (4) Date: Sep. 11, 2009

(87) PCT Pub. No.: WO2007/150020
PCT Pub. Date: Dec. 27, 2007

(65) Prior Publication Data

US 2010/0003266 A1 Jan. 7, 2010

Related U.S. Application Data

(60) Provisional application No. 60/816,015, filed on Jun. 23, 2006.

(51) Int. Cl.
*A61K 39/395* (2006.01)
*C07K 16/00* (2006.01)
*C07H 21/00* (2006.01)
*C12N 15/63* (2006.01)

(52) U.S. Cl. .................. 530/391.7; 530/391.1; 435/188; 435/320.1; 435/325; 424/178.1; 536/23.4

(58) Field of Classification Search ........................ None
See application file for complete search history.

(56) References Cited

U.S. PATENT DOCUMENTS

2005/0070693 A1* 3/2005 Hansen et al. ........... 530/388.22
2010/0266620 A1* 10/2010 Sun ........................... 424/178.1

FOREIGN PATENT DOCUMENTS

WO 9324630 12/1993

OTHER PUBLICATIONS

Chu, C. T. and Pizzo, S. V., "Receptor-mediated antigen delivery into macrophages, Complexing antigen to alpha 2-macroglobulin enhances presentation to T cells," *Journal of Immunology*, vol. 150(1), pp. 48-58, Jan. 1, 1993.

Chu, C. T. et al, "Adjuvant-free in vivo targeting. Antigen delivery by alpha 2-macroglobulin enhances antibody formation,"*Journal of Immunology*, vol. 152(4), pp. 1538-1545, Feb. 15, 1994.

Mitsuda, S. et al., "A receptor-mediated antigen delivery and incorporation system. Administration of alpha 2-macroglobulin-cytochrome c conjugate induced high concentrations of antibodies against cytochrome c in mice," *Biochemical Biophysics Research Communication*, vol. 191(3), pp. 1326-1331, Mar. 31, 1993.

Mitsuda, S. et al., "Receptor-linked antigen delivery system. Importance of autologous alpha 2-macroglobulin in the development of peptide vaccine,"*Biochemical Biophysics Research Communication*, vol. 216(1), pp. 399-405, Nov. 2, 1995.

Osada, T. et al., "Antibodies against viral proteins can be produced effectively in response to the increased uptake of alpha 2-macroglobulin: viral protein conjugate by macrophages," *Biochemical Biophysics Research Communication*, vol. 150(2), pp. 883-889, Jan. 29, 1988.

International Search Report dated Nov. 22, 2007 for International Application No. PCT/US2007/071875.

K.M. Wilson, et al., "Simplified conjugation chemistry for coupling peptides to F(ab') fragments: autologous red cell agglutination assay for HIV-1 antibodies," Journal of Immunological Methods,1994, pp. 267-273, vol. 175.

Ojan Dolezal, et al., "*Escherichia coli* expression of a bifunctional Fab-peptide epitope reagent for the rapid diagnosis of HIV-1 and HIV-2," Immunotechnology, 1995, pp. 197-209, vol. 1.

Kim M. Wilson, et al., "Rapid whole blood assay for HIV-1 seropositivity using an Fab-peptide conjugate," Journal of Immunological Methods, 1991, pp. 111-119, vol. 138, Elsevier Science Publishers B.V.

Glenn G. Lilley, et al., "Recombinant single-chain antibody peptide conjugates expressed in *Escherichia coli* for the rapid diagnosis of HIV," Journal of Immunological Methods, 1994, pp. 211-226, vol. 171.

D. Rylatt, et al., "A Rapid Test for Endotoxin in Whole Blood," Bacterial Endotoxins: Lipopolysaccharides From Genes to Therapy, 1995, pp. 273-284, Wiley-Liss, Inc.

Communication and Supplemental Search Report for EP 07798929.1, (Feb. 2011).

* cited by examiner

*Primary Examiner* — Sharon Wen
(74) *Attorney, Agent, or Firm* — Duane Morris LLP

(57) ABSTRACT

Disclosed herein are materials and methods related to vaccines. Materials and methods for delivery of immunogens to the reticuloendothelial system via non-circulating lymphoid cells are provided.

23 Claims, 2 Drawing Sheets

| | 1 | 2 | 3 | 4 | 5 | 6 | 7 | 8 | 9 | 10 |
|---|---|---|---|---|---|---|---|---|---|---|
| pmol b-Ab | | | 12.5 | 12.5 | 12.5 | 12.5 | 12.5 | 12.5 | 12.5 | |
| pmol StAv | 40 | 40 | 40 | | 10 | 20 | 25 | 30 | 40 | 25 |
| pmol M2e | | 120 | 120 | | | | | | | |
| pmol b-M2e | | | | | 30 | 60 | 75 | 90 | 120 | 75 |

TARGETED IMMUNE CONJUGATE COMPRISING AN ANTIBODY TO GLYCOPHORIN A AND A M2E PEPTIDE

This application is a national stage entry of PCT/US07/71875, filed Jun. 22, 2007, which claims benefit of provisional application, U.S. Ser. No. 60/816,015, filed Jun. 23, 2006.

SEQUENCE LISTING

The instant application contains a Sequence Listing which has been submitted in ASCII format via EFS-Web and is hereby incorporated by reference in its entirety. Said ASCII copy, created on May 18, 2012, is named F5733002.txt and is 3,127 bytes in size.

TECHNICAL FIELD

This invention relates to materials and methods involved in immunotherapy.

BACKGROUND

Vaccination is one of the most important medical interventions for preventing disease. The purpose of vaccination is to induce an optimal immune response that provides preventive or therapeutic benefit to the host. Vaccines typically contain one or more immunogens (IMGs) that are harmless variants or derivatives of pathogens, which act to stimulate the immune system to mount defenses against the actual pathogen. There are many types of immunogens (IMGs), ranging from attenuated or killed microorganisms, microbial extracts, whole proteins, polysaccharides, and peptides. Some IMGs are very effective inducers of the desired immune response, while others require the co-administration of non-specific immune stimulants, or adjuvants, or the coupling of the IMG to a carrier protein or microparticulate substances. Still other IMGs are inherently poor at inducing effective immune responses, despite combination with adjuvants and repeated boosts. Many of these inherently weak immunogens are involved in diseases e.g., influenza and cancer, that remain major causes of human morbidity and mortality. There is a continuing need for effective and more potent vaccines, particularly those with the capacity to stimulate a robust immune response against weakly immunogenic targets.

SUMMARY

Disclosed herein are immune conjugates that are useful for inducing or enhancing an immune response against an antigen. Accordingly, disclosed are immune conjugates that include a ligand which binds specifically to a cell surface molecule on a circulating non-lymphoid cell, and an immunogen coupled to the ligand, wherein the immune conjugate, when administered to an individual, induces or enhances an immune response against the immunogen. In one embodiment, the immune conjugate includes a ligand which binds specifically to a cell surface molecule on a circulating non-lymphoid cell, wherein the molecule is selected from the group consisting of CR2, glycophorin A, band 3, Ter-119, blood group antigen H, blood group antigen A, blood group antigen B, CD41a, CD14, CD56, CD66d, CD83, CMKLR1, and BDCA-4; and an immunogen coupled to the ligand, where the immune conjugate, when administered to an individual, induces or enhances an immune response against the immunogen.

A circulating non-lymphoid cell can be any cell that circulates through the body of a mammal in the blood and/or lymph system; and is not a B lymphocyte or a T lymphocyte. The circulating non-lymphoid cell can be, for example, a red blood cell, a platelet, a natural killer cell, a monocyte, a granulocyte or a plasmacytoid dendritic cell. In one embodiment, the circulating non-lymphoid cell is a red blood cell. In another embodiment, the circulating non-lymphoid cell is a platelet. The circulating non-lymphoid cell can be derived from any mammal, e.g., humans, a non-human primates, cattle, horses, pigs, sheep, goats, deer, elk, dogs, cats, mustelids, rabbits, guinea pigs, hamsters, rats, or mice.

The cell-surface molecule can be any molecule that is differentially expressed on circulating non-lymphoid cells relative to the levels of the same molecule on a cell type that is not a circulating non-lymphoid cell. The cell-surface molecule can be a polypeptide, a carbohydrate, a phospholipid, or a glycolipid.

In one embodiment, the cell surface molecule can be a molecule on the surface of a red blood cell, including, for example, complement receptor 2 (CR2), glycophorin A (CD235A), band 3 (CD233), TER-119, the ABO blood group antigens, e.g., blood group antigen A, blood group antigen B, blood group antigen H, and phosphatidyl serine. In another embodiment, the cell surface molecule can be a molecule on the surface of a platelet, including, for example, gpIIb/IIIa (CD41a), CD42d, CD61, CD62P (P-selectin) and CD151. In another embodiment, the cell surface molecule can be a molecule on the surface of a natural killer (NK) cell, including, for example, CD56 (NCAM, Leu-19, NKH1). In another embodiment, the cell surface molecule can be a molecule on the surface of a monocyte, including, for example, CD14 (LPS-receptor). In another embodiment, the cell surface molecule can be a molecule on the surface of a granulocyte, including, for example, CD66d (CGM1, a member of the CEA family). In another embodiment, the cell surface molecule can be a molecule on the surface of a plasmacytoid dendritic cell, including, for example, CMKLR1 (serpentine chemokine-like receptor 1), BDCA-2 (CD303) and BDCA-4 (CD304).

The ligand can be any molecule capable of binding a specific cell surface molecule on a circulating non-lymphoid cell. A ligand can include, for example, a polypeptide, a carbohydrate, glycolipid or biomimetic of a polypeptide, carbohydrate or glycolipid, as long as the ligand binds specifically to a cell surface molecule that is differentially expressed on a circulating non-lymphoid cell.

A ligand can be a polypeptide, provided that it is not C3d, a heat shock protein, muramyl dipeptide, or muramyl tripeptide.

In one embodiment, a polypeptide ligand can be an antibody. The antibody can be a monoclonal antibody, a polyclonal antibody, a holoantibody, a single chain variable fragment immunoglobulin, or a chimeric molecule that contains the constant region of an immunoglobulin and cell-binding sequences from a different source grafted in place of the immunoglobulin variable regions. The antibody can be, for example, an antibody that recognizes targets on red blood cells e.g., complement receptor 2 (CR2), glycophorin A (CD235A), band 3 (CD233), TER-119, blood group antigen A, blood group antigen B, and blood group antigen H. The antibody can be, for example, an antibody that recognizes targets on platelets, e.g. gpIIb/IIIa (CD41a), CD42d, CD61, CD62P (P-selectin) and CD151. The antibody can be, for example, an antibody that recognizes targets on monocytes, e.g., CD14. The antibody can be, for example, an antibody that recognizes targets on granulocytes, e.g., CD66d. The antibody can be, for example, an antibody that recognizes targets on NK cells, e.g., CD56. The antibody can be, for example, an antibody that recognizes targets on plasmacytoid dendritic cells, e.g., CMKLR1, BDCA-2 (CD303) and BDCA-4 (CD304).

A ligand can also be a polypeptide that is not an immunoglobulin, including for example, the erythrocyte-binding antigen 175 (EBA-175) of *Plasmodium falciparum* or a fragment of EBA-175 that binds to a red blood cell, for example, SEQ ID NO:7, a complement fragment that binds to CR2, for example, C4b, C3b, iC3b, C1q, C3d or a peptide derived from these complement fragments, e.g., C3 residues 1201-1214; or a lectin, e.g., a glycoprotein that recognizes blood group antigen A, blood group antigen B or blood group antigen H.

The polypeptide ligand can include post-translational modifications, e.g., biotinylation, glycosylation, acetylation, alkylation, isoprenylation, lipoylation, phosphorylation.

In another embodiment a ligand can also be a carbohydrate or glycolipid, including, for example, bacterial lipopolysaccharide or a fragment of it, microbial products bound by Toll-like receptors, bacterial diacyl and triacyl lipopeptides, lipoteichoic acid or zymosan.

In another embodiment, a ligand can be a nucleic acid, including, for example, single- and double-stranded viral RNA and CpG DNA.

The immunogen can be any molecule capable of eliciting a functional immune response in a mature T or a B lymphocyte or a precursor of a T or a B lymphocyte. Immunogens can include polypeptides, carbohydrates, glycolipids, haptens or biomimetics thereof. The immunogen can be a molecule expressed or released by an infectious agent, including, for example, viruses, viroids, bacteria, fungi, prions or parasites. An infectious agent can include for example, Orthomyxoviridae, e.g., influenza viruses, including the strain A (H5N1), Rhadboviridae, Hepadnaviridae, e.g., hepatitis B, Picornaviridae, e.g., hepatitis A, Flaviviridae, e.g., hepatitis C; Retroviridae, e.g., human immunodeficiency viruses HIV1 and HIV2, Togaviridae, Bunyaviridae, e.g., hantavirus; Paramyxoviridae, Herpesviridae, Arenaviridae, e.g., lassa virus; Reoviridae; *Bacillus anthracis, Clostridium botulinum, Salmonella enteriditis, Escherichia coli*, including *E. coli* O157:H7, *Streptococcus pneumoniae, Staphylococcus aureus, Aspergillus, Stachybotrys, Candida, Cryptosporidium, Toxoplasma*, and *Plasmodium falciparum*.

Immunogens derived from pathogenic organisms can include, for example, influenza A M2 protein, hepatitis B surface antigen, HBV preS1 protein, HIV tat, HIV gp120, anthrax protective antigen, botulinum toxin, and *Streptococcus pneumoniae* pneumococcal polysaccharides. An influenza M2 protein antigen can be the ectodomain peptide M2e, for example SEQ ID NO: 1, or a variant of the ectodomain peptide M2e, for example, SEQ ID NO: 3 or SEQ ID 4. An HBV preS1 protein can include the preS1 protein peptide 35-49, for example SEQ ID NO:2.

The immunogen can also be a molecule expressed by a mammal. For example, an immunogen can be a molecule whose expression is correlated with a particular disease for example, cancer or neurodegenerative disease. The immunogen can be a tumor-associated antigen (TAA), including for example, MART-1, Muc-1, MAGE, RAGE, or CEA. In another embodiment, the immunogen can be an antigen that is involved in the initiation or progression of neurodegenerative diseases, e.g. Alzheimer's disease and Transmissible Spongiform Encephalopathies (TSEs), including for example, beta-amyloid, tau protein, alpha synuclein, or a prion-related protein. In another embodiment, the immunogen can be a germ cell antigen, including for example, sperm adhesion molecule 1 (SPAM-1), and human intra-acrosomal protein. In another embodiment, the immunogen can be a non-toxic variant of a toxic substance, including for example, ricin, botulinum toxins A, B, C, D, E, F and G. nicotine, or a drug of abuse such as an opiate or opiate derivative.

The ligand and the immunogen are connected by a linker. A linker can be any reagent, molecule or macromolecule that connects the ligand and the immunogen such that a) the immune complex is stable under physiological conditions; b) the connection between the linker and the ligand does not alter the ability of the ligand to bind to its target on the surface of a circulating non-lymphoid cell; and c) the connection between the linker and the immunogen does not abolish the capacity of the immunogen to induce an effective immune response in a host against an infectious agent, cell or molecule on which the immunogen is naturally found.

In one embodiment, a linker can be a peptide bond. The ligand and the immunogen can be a fusion polypeptide comprising one or more amino acid segments from the ligand and one or more amino acid segments from the immunogen. The amino acid segments of the ligand can be contiguous with the amino acid segments of the immunogen or they can be separated by amino acids inserted as a structural spacer. A spacer segment can be one or more amino acids. The one or more amino acids can include amino acids that are the same or that are different. Also encompassed are nucleic acids comprising a nucleotide sequence that encodes the fusion proteins, a vector (e.g., a vector that includes a transcriptional regulatory element (TRE) operably linked to the nucleotide sequence) containing the nucleic acid, and a cell (e.g. a prokaryotic cell or a eukaryotic cell) containing the vector.

In another embodiment, the ligand and immunogen can be obtained separately, either through chemical synthesis or synthesis in vivo, purified and then linked non-covalently or covalently. The non-covalent linkage can be a for example, a biotin-avidin (or streptavidin) linkage. The covalent linkage can be through a chemical cross-linking agent, for example, a homobifunctional cross-linking reagent or a heterobifunctional cross-linking reagent. In another embodiment, the ligand and the immunogen can be connected through a linking polymer, including, for example, linear or branched polymers or co-polymers (e.g., polyalkylene, poly(ethylene-lysine), polymethacrylate, polyamino acids, poly- or oligosaccharides, or dendrimers).

In another embodiment, the ligand and the immunogen can be connected through a microparticle, including, for example, micelles, liposomes, fullerenes, nanotubes, or other colloidal complexes such as lipoproteins. The ligand and the immunogen can be attached to the linking molecule or microparticle through a non-covalent high affinity linkage, e.g., avidin-biotin high affinity binding, adsorbed or incorporated into a hydrophobic microparticle by hydrophobic affinity, or covalent chemical cross-linking techniques.

The immune conjugates provided herein can include one or more of the same ligands or any combination of different ligands. The immune conjugates can also include one or more of the same immunogens or any combination of different immunogens.

Also provided are methods and materials for inducing or enhancing an immune response in a mammal, the method comprising administering to the mammal an effective amount of a composition comprising an immune conjugate that includes a ligand which binds specifically to a cell surface molecule on a circulating non-lymphoid cell, and an immunogen coupled to the ligand, wherein the immune conjugate, when administered to an individual, induces or enhances an immune response against the immunogen. In one embodiment, the immune conjugate includes a ligand which binds specifically to a cell surface molecule on a circulating non-lymphoid cell, wherein the molecule is selected from the group consisting of CR2, glycophorin A, band 3, Ter-119, blood group antigen H, blood group antigen A, blood group antigen B, CD41a, CD14, CD56, CD66d, CD83, CMKLR1, and BDCA-4; and an immunogen coupled to the ligand, where the immune conjugate, when administered to an individual, induces or enhances an immune response against the immunogen.

The mammals can be, for example, humans, non-human primates, horses, cattle, pigs, sheep, deer, elk, goats, dogs, cats, mustelids, rabbits, guinea pigs, hamsters, rats, and mice. The mammal can have, be likely to have, or be at risk for having, an infectious disease, e.g., a viral disease, a bacterial disease, a protozooal disease, or a fungal disease. Infectious diseases can include, for example, influenza, HIV-AIDS, hepatitis, botulism, smallpox, viral hemorrhagic fevers, gastrointestinal disease induced by pathogenic forms of *E. coli, Salmonella* and *Shigella, Staphylococcal* infection, trypanosomiasis, and malaria. Alternatively, the mammal can have, be likely to have, or be at risk for having, a proliferative cell disease, e.g., a cancer such as a neural tissue cancer, melanoma, breast cancer, lung cancer, a gastrointestinal cancer, ovarian cancer, testicular cancer, lung cancer, prostate cancer, cervical cancer, bladder cancer, vaginal cancer, liver cancer, renal cancer, bone cancer, a hematological cell cancer, or a vascular tissue cancer. In another embodiment, the mammal can have, be likely to have, or be at risk for having, a neurodegenerative disease, e.g., Alzheimer's disease or a Transmissible Spongiform Encephalopathy (TSE).

In another embodiment, methods and materials for inducing or enhancing an immune response in a mammal against a germ cell antigen are provided. In a further embodiment, methods and materials for inducing or enhancing an immune response in a mammal against toxic substances, e.g., ricin, botulinum toxin, nicotine and drugs of abuse are provided.

Also provided are compositions featuring immune conjugates that include a ligand which binds specifically to a cell surface molecule on a circulating non-lymphoid cell, and an immunogen coupled to the ligand, wherein the immune conjugate, when administered to an individual, induces or enhances an immune response against the immunogen in a pharmaceutically acceptable carrier or excipient. In another embodiment, the composition can include an adjuvant.

Also provided are articles of manufacture that can include immune conjugates as described herein. An article of manufacture can include, for example, one or more immune conjugates. In addition, an article of manufacture further may include, for example, packaging materials, instructions for use, buffers or other control reagents for treating or monitoring the condition for which prophylaxis or treatment is required.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
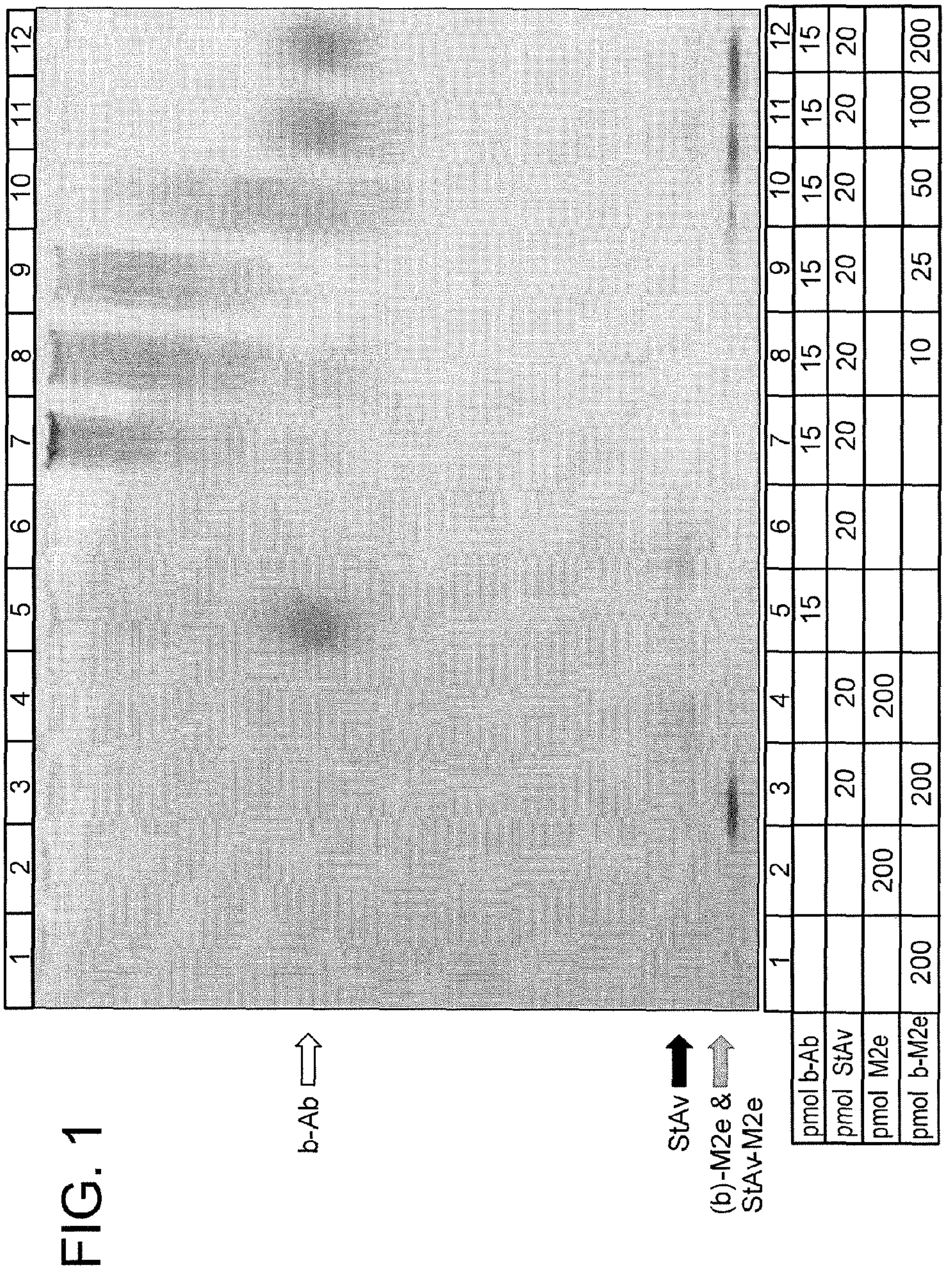
FIG. 1 depicts the electrophoretic mobility of tripartite immune conjugates containing biotinylated antibody, streptavidin, and varying amounts of biotinylated M2e peptide (SEQ ID NO:1).

The mammalian immune system mounts two different types of responses to immunogens (IMGs), humoral and cellular. The humoral response, mediated by B lymphocytes, defends primarily against extracellular pathogens through the production of circulating antibodies that mark foreign cells and molecules for destruction by other specialized cells and proteins. The cellular response, mediated by T lymphocytes, defends predominantly against intracellular pathogens and cancers by directly binding to and destroying the infected or cancerous cells. Both responses depend upon specialized cells that internalize through endocytosis, pinocytosis or phagocytosis, and process IMGs; fragments of the IMGs are then presented to T lymphocytes, which in turn, help to trigger B-lymphoctye responses against the immunogens and/or the T cells to attack the target directly.

The phagocytic cells that function as antigen-presenting cells (APCs) are part of the reticuloendothelial system (RES). The RES is a diffuse system comprised of circulating and tissue-fixed cells including monocytes, macrophages, dendritic cells, Kupffer cells in the liver, Langerhans cells in the skin and microglial cells in the brain Several tissues and organs, by virtue of their wealth of phagocytic and specialized endothelial cells, comprise critical locations for the clearance and antigen presentation functions of the RES. These include the liver, spleen, bone marrow and lymphatic tissues. The RES plays an important role in clearing potentially harmful materials from the blood including micro-organisms, bacterial endotoxins, immune complexes, tumor cells and senescent and damaged cells of the blood and lymph systems. The cells that cycle through the RES, e.g. red blood cells (or erythrocytes), platelets, natural killer cells, monocytes, granulocytes, and plasmacytoid dendritic cells, serve as carriers of foreign materials, which may be stripped off in RES organs. If the load of foreign material on the surface of the circulating cells is very dense, these cells themselves can be targets for phagocytic activity. In addition, as circulating cells age, they acquire surface markers that cause them to be captured by the RES, removed from circulation and destroyed by phagocytosis, resulting in the degradation of the circulating cell components and their surface-bound materials. Once these cells have been phagocytized, any fragments of macromolecules they originally contained, either endogenously expressed molecules or exogenous molecules that were opsonized to the cell surface can potentially be presented to T lymphocytes. Thus, molecules bound to red blood cells, platelets, natural killer cells, monocytes, granulocytes, and plasmacytoid dendritic cells can function as immunogens.

Disclosed herein are materials and methods for the specific delivery of immunogens to the reticuloendothelial system via circulating non-lymphoid cells. In particular, targeted immune conjugates are provided that specifically bind to circulating non-lymphoid cells, e.g., red blood cells, platelets, natural killer cells, monocytes, granulocytes, and plasmacytoid dendritic cells, that are cleared through the RES. Thus, the circulating non-lymphoid cells act as vehicles for the specific delivery of IMGs to the RES and thereby to the immune system. As used herein, the term "targeting immune conjugate" includes a ligand which binds specifically to a cell surface molecule on a circulating non-lymphoid cell coupled to an IMG, where the targeted immune conjugate, when administered to an individual, induces or enhances an immune response against the IMG. Also provided are methods of treatment using targeted immune conjugates. Targeted immune conjugates provide injectable vaccines for efficient immunization against weakly immunogenic IMGs.

II. Compositions

The targeting immune conjugates provided herein have the general formula:

$$(L)_y\text{-X-}(IMG)_z$$

wherein L is a ligand which binds specifically to a cell surface molecule on a circulating non-lymphoid cell; X is a linker; IMG is an immunogen, and y and z are integers having a value of one or greater than one.

Circulating Non-Lymphoid Cells and Targets

As used herein, a circulating non-lymphoid cell can be any cell that a) circulates through the body of a mammal in the blood and/or lymph system; and b) is not a B lymphocyte or a T lymphocyte. Thus, circulating non-lymphoid cells include erythrocytes, i.e., red blood cells; platelets; natural killer cells; monocytes; granulocytes, i.e., neutrophils, eosinophils, and basophils; and plasmcytoid dendritic cells.

B and T lymphocytes are ultimately derived from hematopoietic stem cells and perform the principal functions of the immune system. T lymphocytes mature through the thymus and are generally identified by their expression of CD3 (which is associated with the T cell receptor) and either CD4 or CD8. CD8-expressing (or CD8+) T cells are principally involved with direct cell killing, or cytotoxicity. CD4+ T cells are primarily regulatory cells which stimulate and suppress immune responses as needed. B lymphocytes are characterized by their expression of CD19 or CD20, among other surface markers, and they are responsible for antibody production. B cells are also effective antigen presenting cells.

Erythrocytes, also known as red blood cells, are the most abundant cell type in mammalian blood. They are small disc-shaped, anucleated, biconcave cells whose primary function is to carry oxygen and carbon dioxide to and from the tissues. Red blood cells express a distinctive complement of cell surface markers, including the human blood group antigens, glycophorin, band 3 and the Lewis antigens.

Platelets are derived from megakaryocytes, they are centrally involved in blood clotting, and can be identified by their surface expression of CD41a (or gpIIb/IIIa). Natural killer cells, also referred to as large granular lymphocytes, are derived from the bone marrow and do not express T-cell antigen receptors (TCR), the pan-T marker CD3 or surface immunoglobulins (Ig) B cell receptor, but typically express the surface markers CD16 (FcγRIII) and CD56. Monocytes are derived from myeloid stem cells and are found primarily in the circulation. They are competent phagocytes. Upon their binding of pathogens and/or stimulation by various cytokines, monocytes mature into macrophages, which are even more avid phagocytes and producers of many cytokines, degradative enzymes and other molecules that mediate inflammatory reactions. Macrophages are generally found bound to vascular endothelium or within various tissues. Monocytes (and macrophages) are characterized by the surface expression of CD14, among other markers.

Granulocytes are also derived from myeloid stem cells and are characterized by the presence of abundant granules in their cytoplasm; different classes of granulocytes, e.g., eosinophils, basophils and neutrophils, are distinguished by their ability stain with eosin, basophilic dyes or neither, respectively. Eosinophils are involved in defense against parasitic pathogens and allergens; basophils are also involved in allergic reactions. Neutrophils are early and aggressive phagocytes at the site of infections and release products that induce inflammatory reactions.

Plasmacytoid dendritic cells (pDC) are distinct from myeloid dendritic cells. Both are found in the circulation and in tissues. pDC are an important link between the innate and adaptive immune responses, in particular in mounting antiviral immune responses. They produce abundant interferons and can be identified by the surface marker BDCA-2 (CD303).

The circulating non-lymphoid cells can be derived from any mammal, e.g., humans, a non-human primates, cattle, horses, pigs, sheep, goats, deer, elk, dogs, cats, mustelids, rabbits, guinea pigs, hamsters, rats, or mice.

Any cell-surface molecule that is differentially expressed on circulating non-lymphoid cells relative to the levels of the same molecule on a cell type that is not a circulating non-lymphoid cell is a suitable target for the ligand. The cell-surface molecule can be a polypeptide, a carbohydrate, or a glycolipid. Full-length molecules, epitopes, analogs, mutants, and functional fragments thereof are encompassed by this definition. A "functional fragment" of a molecule is a fragment of the molecule that is smaller (shorter where the molecule is a polypeptide) than the molecule per se but has at least 10% (e.g., 10%, 20%, 30%, 40%, 50%, 60%, 70%, 80%, 90%, 95%, 98%, 99%, 99.5%, 100% or even more) of the ligand-binding activity of the molecule per se.

Typically, a cell-surface molecule on a circulating non-lymphoid cell can be classified as being differentially expressed if the molecule is present at a level that is greater than the average level observed in cells that are not circulating non-lymphoid cells if the expression levels differ by at least 50% (e.g. 50, 100, 200, 300% or more). Any method can be used to determine whether or not a specific gene product is expressed at a level that is greater or less than the average level of expression observed in control cells. The level of expression of a cell surface polypeptide can be measured using any method such as immuno-based assays (e.g., immunofluorescence, flow cytometry, ELISA), western blotting, or polyacrylamide gel electrophoresis with silver staining. Levels of particular carbohydrates or lipids can be measured by immunodetection e.g., ELISA, flow cytometry, or immunostaining using fluorochrome- or radioisotope-labeled antibodies or lectins. In some embodiments, the level of expression from a particular gene can be measured by assessing the level of mRNA expression from the gene. Levels of mRNA expression can be evaluated using, without limitation, northern blotting, slot blotting, quantitative reverse transcriptase polymerase chain reaction (RT-PCR), or chip hybridization techniques. Such methods can be used to determine simultaneously the relative expression levels of multiple mRNAs.

Examples of targets on red blood cells include, without limitation, complement receptor 2 (CR2), glycophorin A (CD235A), band 3 (CD233), TER-119 (Kina et al., Br. J. Hematol. 109: 280-7, 2000), the ABO blood group antigens, e.g., blood group antigen A, blood group antigen B, blood group antigen H, and phosphatidyl serine (Hematology: Basic Principles and Practice, R. Hoffman, 2005, 4th ed. New York: Churchill-Livingstone). One useful red blood cell target is TER-119, a region selectively bound by the antibody, anti-TER-119 and which corresponds to the extracellular domain of glycophorin A. Suitable platelet targets includes gpIIb/IIIa (CD41a), CD42d, CD61, CD62P (P-selectin) and CD151. Natural killer cell targets include, for example, CD56 (NCAM, Leu-19, HNK1). Monocyte and granulocyte targets include, for example, CD14 (LPS-receptor) and CD66d (CGM1, a member of the CEA family), respectively. Plasmacytoid dendritic cell targets include, for example, CMKLR1 (serpentine chemokine-like receptor 1), BDCA-2 (CD303) and BDCA-4 (CD304) (Kuby Immunology, J. Kuby et al., edt., 2002, $5^{th}$ edition, W.H. Freeman & Co.).

Ligands

The term "ligand" as used herein refers to a molecule capable of binding a specific cell surface molecule on a circulating non-lymphoid cell. A ligand can be a polypeptide, a carbohydrate, glycolipid or biomimetic of a polypeptide, carbohydrate or glycolipid, as long as the ligand binds specifically to a cell surface molecule that is differentially expressed on a circulating non-lymphoid cell.

As defined herein, ligands are defined to be "specifically binding" if: 1) they exhibit a threshold level of binding activity, and/or 2) they do not significantly cross-react with related target molecules. The binding affinity of a ligand can be readily determined by one of ordinary skill in the art, for example, by Scatchard analysis (Scatchard, Ann. NY Acad. Sci. 51: 660-672, 1949). For example, a ligand disclosed herein can bind to its target with at least 1.5-fold, 2-fold, 5-fold, 10-fold, 100-fold, 103-fold, 104-fold, 105-fold, 106-fold or greater affinity for the target than for a closely related or unrelated polypeptide. A ligand can bind its target with high affinity ($10^{-4}$M or less, $10^{-7}$M or less, $10^{-9}$M or less, or with subnanomolar affinity (0.9, 0.8, 0.7, 0.6, 0.5, 0.4, 0.3, 0.2, 0.1 nM or even less). Ligands can also be described or specified in terms of their binding affinity to a target, for example, binding affinities include those with a Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$M, $5\times10^{-6}$ M, $10^{-6}$ M, $5\times10^{-7}$ M, $10^{-7}$ M, $5\times10^{-8}$M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M, or less.

In some embodiments, the ligands disclosed herein do not bind to known related molecules. In other embodiments, the ligands disclosed herein can bind to orthologs, homologs, paralogs or variants, or combinations and subcombinations thereof, of their targets.

As defined herein, a ligand that specifically binds to circulating non-lymphoid cells is a ligand the binds to circulating non-lymphoid cells and does not significantly bind to lymphoid cells. For example, an immune conjugate that includes a ligand that specifically binds to red blood cells will bind to red blood cells and not significantly bind to other circulating cells, e.g., lymphocytes, platelets, natural killer cells, monocytes, granulocytes or dendritic cells. In another example, an immune conjugate that includes a ligand that specifically binds to platelets will bind to platelets and not significantly bind to other circulating cells, e.g., lymphoid cells, red blood cells, natural killer cells, monocytes, granulocytes or dendritic cells.

Ligands may be screened against known related target polypeptides to isolate a ligand that specifically binds the target. For example, a ligand specific to a target will flow through an affinity chromatography column comprising other closely related target molecules adhered to insoluble matrix under appropriate buffer conditions. Such screening allows isolation of ligands non-crossreactive to closely related targets (Antibodies: A Laboratory Manual, Harlow and Lane (eds.), Cold Spring Harbor Laboratory Press, 1988; Current Protocols in Immunology, Cooligan et al. (eds.), National Institutes of Health, John Wiley and Sons, Inc., 1995). Screening and isolation of specific antibodies is well known in the art (see, Fundamental Immunology, W. Paul (ed.), Raven Press, 1993; Getzoff et al., Adv. in Immunol. 43: 1-98, 1988; Monoclonal Antibodies: Principles and Practice, Goding, J. W. (ed.), Academic Press Ltd., 1996; Benjamin et al., Am. Rev. Immunol. 2: 67-101, 1984). Representative examples of such assays include: concurrent immunoelectrophoresis, radioimmunoassay (RIA), radioimmunoprecipitation, flow cytometry, FACS, enzyme-linked immunosorbent assay (ELISA), dot blot or western blot assay, inhibition or competition assay, and sandwich assay.

A ligand can be a polypeptide, provided that it is not C3d, a heat shock protein, muramyl dipeptide, or muramyl tripeptide. The term "polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, dicysteine, ester or ether bonds. The term "amino acid" refers to natural and/or unnatural or synthetic amino acids, including D/L optical isomers. Full-length proteins, analogs, mutants, and fragments thereof are encompassed by this definition.

The amino acid sequence of the ligands disclosed herein can be identical to the wild-type sequences of appropriate components. Alternatively, any of the components can contain mutations such as deletions, additions, or substitutions. All that is required is that the variant ligand have at least 5% (e.g., 10%, 20%, 30%, 40%, 50%, 60%, 70%, 80%, 90%, 95%, 99%, 100%, or even more) of the ability of the ligand containing only wild-type sequences to specifically bind the target on the circulating non-lymphoid cell. Substitutions will preferably be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Any method can be used to make a polypeptide including, for example, expression by prokaryotic systems, expression by eukaryotic systems, and chemical synthesis techniques. Any method can be used to purify a polypeptide including, without limitation, fractionation, centrifugation, and chromatography, e.g., gel filtration, ion exchange chromatography, reverse-phase HPLC and immunoaffinity purification.

A suitable polypeptide ligand can be an antibody. In one embodiment, the antibody can be a monoclonal antibody, i.e., homogeneous antibodies of identical antigenic specificity produced by a single clone of antibody-producing cells. In another embodiment, the antibody can be a polyclonal antibody, i.e., heterogenous antibodies that can recognize different epitopes on the same antigen and that are produced by more than one clone of antibody producing cells.

The antibody can include any class of immunoglobulin, e.g. IgG, IgA, IgM; and can be derived from any species e.g., humans, mice, rats, or can be a humanized version of a non-human antibody. An antibody can include, without limitations, a holoantibody, i.e., an antibody that includes one or more of an immunoglobulin monomer units of two heavy and two light chains, a single chain variable fragment immunoglobulin, or a chimeric molecule that contains the constant region of an immunoglobulin and cell-binding sequences from a different source grafted in place of the immunoglobulin variable regions. The cell-binding regions can be from a different antibody, a lectin, a cytokine, a microbial protein fragment or any other molecule that binds the target cell receptor molecule with specificity.

Methods for producing antibodies are well know to those in the art; Antibodies can be purified by chromatographic methods known to those of skill in the art, including ion exchange and gel filtration chromatography (for example, Caine et al., Protein Expr. Purif. (1996) 8(2):159-166). Alternatively or in addition, antibodies can be purchased from commercial sources, for example, Invitrogen (Carlsbad, Calif.); MP Biomedicals (Solon, Ohio); Nventa Biopharmaceuticals (San Diego, Calif.) (formerly Stressgen); Serologicals Corp. (Norcross, Ga.).

The antibody can be, for example, an antibody that recognizes targets on red blood cells, including for example, without limitation, glycophorin A (CD235A), band 3 (CD233), TER-119, blood group antigen A, blood group antigen B, and blood group antigen H. One useful antibody is anti-TER-119, which specifically binds to TER-119, a region corresponding to the extracellular domain of glycophorin A. Other suitable antibodies include, without limitation, antibodies that recognize targets on platelets, e.g., gpIIb/IIIa (CD41a), CD42d, CD61, CD62P (P-selectin) and CD151; monocytes, e.g., CD14; NK cells, e.g., CD56; granulocytes, e.g., CD66d; and plasmacytoid dendritic cells, e.g., CMKLR1, BDCA-2 (CD303) and BDCA-4 (CD304).

A ligand can also be a polypeptide that is not an immunoglobulin. One non-immunoglobulin type ligand can be the erythrocyte-binding antigen 175 (EBA-175) of *Plasmodium falciparum*, which specifically binds the red blood cell surface protein band 3, or a fragment of EBA-175 that binds to a red blood cell, for example EBA-175 peptide 1085-96, SEQ ID NO:7. Another polypeptide ligand can also be a complement fragment that binds to CR2, for example, C4b, C3b, iC3b, C1q or a peptide derived from the complement fragments, e.g., C3 residues 1201-1214 (Tsokos et al., Journal of Immunol. 144: 1640-45, 1990) or residues 727-768 (Becherer, Biochemistry 31(6):1787-94, 1992). A polypeptide ligand can also be a lectin, e.g. a glycoprotein that recognizes blood group antigen A, blood group antigen B or blood group antigen H.

A ligand can also be a peptidomimetic, a small protein-like chain containing non-peptidic structural elements that is capable of mimicking or antagonizing the biological action(s) of a natural parent peptide. Peptidomimetic compounds are synthetic, non-peptide compounds having a three-dimensional conformation (i.e., a "peptide motif") that is substantially the same as the three-dimensional conformation of a selected peptide. The peptide motif provides the peptidomimetic compound with the ability to bind the ligand in a manner qualitatively identical to that of the parent peptide from which the peptiomimetic was derived. Peptidomimetic compounds can have additional characteristics that enhance their therapeutic utility, such as increased prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Any peptidomimetic that binds specifically and selectively to a cell surface molecule that is differentially expressed on a circulating non-lymphoid cell can be used. Examples of useful peptidomimetics include those that mimic the ability of antibodies that recognize, for example, complement receptor 1 (CR1), complement receptor 2 (CR2), glycophorin A (CD235A), band 3 (CD233), TER-119, blood group antigen A, blood group antigen B, and blood group antigen H, gpIIb/IIIa (CD41a), CD42d, CD61, CD62P (P-selectin), CD151, CD14, CD56, CD66d, CMKLR1 and BDCA-2.

The polypeptide can include post-translational modifications, i.e., chemical modification of the polypeptide after its synthesis. Chemical modifications can be naturally occurring modifications made in vivo following translation of the mRNA encoding the polypeptide or synthetic modifications made in vitro. A polypeptide can include one or more post-translational modifications, in any combination of naturally occurring, i.e., in vivo, and synthetic modifications made in vitro. Examples of post-translational modifications include, but are not limited to, biotinylation, e.g., acylation of lysine or other reactive amino acid residues with a biotin molecule; glycosylation, e.g., addition of a glycosyl group to either asparagines, hydroxylysine, serine or threonine residues to generate a glycoprotein or glycopeptide; acetylation, e.g. the addition of an acetyl group, typically at the N-terminus of a polypeptide; alkylation, e.g., the addition of an alkyl group; isoprenylation, e.g., the addition of an isoprenoid group; lipoylation, e.g. attachment of a lipoate moeity; phosphorylation, e.g. addition of a phosphate group to serine, tyrosine, threonine or histidine.

A highly suitable post-translational modification can be biotinylation. Biotin, also known as vitamin H or B7 is a water-soluble B-complex vitamin that binds avidin or streptavidin with very high affinity ($10^{-15}$M). Both egg avidin and bacterial streptavidin have 4 biotin-binding sites and thus can serve to couple several biotinylated ligands or to couple biotinylated ligand(s) to other biotinylated molecules (e.g., IMGs). Polypeptides can be covalently linked to one or more biotin molecules through primary amines, e.g. lysine and N-terminus), carboxyl groups found on aspartic- and glutamic-acid residues and at the C-terminus, sulfhydryl groups, or carbohydrate modifications on glycoproteins. Methods for derivatizing polypeptides with biotin are well known in the art and there are many commercial sources for such reagents (e.g. Pierce, Sigma-Aldrich). Any method of biotinylation can be used that preserves the ability of the ligand to bind to its target on the non-circulating lymphoid cell. For example, desirable biotinlyation methods would modify residues in the Fc portion of the antibody without compromising the immunoreactivity of the antibody. Polypeptides derivatized with biotin can then be linked to immunogens through an avidin or streptavidin molecule.

A post-translational modification can be glycosylation, i.e., the addition of saccharides. Glycosylation is typically classified based on the amino acid through which the saccharide linkage occurs and can include: N-linked glycosylation to the amide nitrogen of asparagines side chains, O-linked glycosylation to the hydroxyloxygen of serine and threonine side chains, and C-mannosylation.

A ligand can also be a carbohydrate or glycolipid. Examples of carbohydrate and glycolipid ligands, include, without limitation, bacterial lipopolysaccharide (LPS) or a fragment of it, microbial products bound by Toll-like receptors (TLRs), bacterial diacyl and triacyl lipopeptides and lipoteichoic acid from bacteria, and zymosan from yeast cell walls.

A ligand can also be a nucleic acid. Examples of nucleic acids include, without limitation, single- and double-stranded RNA from viruses, and CpG DNA from bacteria or viruses.

Immunogens

As defined herein, an immunogen is any molecule capable of eliciting a functional immune response (e.g., a cytotoxic or helper T cell response or an antibody producing response) in a T or a B cell.

As used herein, an "effector T lymphocyte" is a T lymphocyte having immunological activity. Such immunological activity can be, without limitation, cytotoxic activity, helper activity, suppressive activity, immune-deviating activity, inflammatory activity, or pro-inflammatory activity. As used herein, an "effector T lymphocyte precursor cell" is a T lymphocyte that, subsequent to activation, has any of the above immunological activities. Activation can occur, without limitation, by recognition of a complex of the relevant immunogenic peptide epitope and the major histocompatibility complex (MHC) molecule by the T cell receptor (TCR) on the effector T lymphocyte or by a non-specific stimulus, e.g., a T cell mitogen such as concanavalin A. Thus, an effector T lymphocyte cell can be a "virgin" T lymphocyte that has never previously been activated or a "memory" T lymphocyte that has previously been activated or the progeny of such a memory T lymphocyte. As used herein, a "cytotoxic T lymphocyte" (CTL) is a T lymphocyte that can kill a target cell expressing on its surface a peptide epitope-MHC molecular complex for which the TCR of the CTL is specific.

As used herein, a "CTL cell" is a T lymphocyte that can, subsequent to activation, kill a target cell expressing on its surface a peptide epitope-MHC molecular complex for which the TCR of the CTL is specific. Activation can be, without limitation, by recognition of the relevant peptide epitope-MHC molecular complex by a TCR on the CTL or by a non-specific stimulus, e.g., a T cell mitogen such as concanavalin A. Thus, a CTL cell can be a "virgin" T lymphocyte that has never previously been activated or a "memory" T lymphocyte that has previously been activated or the progeny of such a memory T lymphocyte.

As used herein, a "helper T lymphocyte" (Th) is a T lymphocyte that provides helper or regulatory activity in an immune response. Such an immune response can be, for example, an antibody-producing response of a B lymphocyte, a response of a CTL precursor cell, or an inflammatory or pro-inflammatory response of a variety of leukocyte types. As used herein, a "Th cell" is a T lymphocyte that, subsequent to activation, provides helper activity in an immune response such as those listed above for Th. Activation can be as indicated above for CTL cells. Furthermore, a Th cell can be a "virgin" T lymphocyte that has never previously been activated or a "memory" T lymphocyte that has previously been activated or the progeny of such a memory T lymphocyte.

As used herein, a B cell is a B lymphocyte that, subsequent to activation, can produce antibody molecules. Activation of a B cell can be, without limitation, by recognition of an antigen by an antigen specific immunoglobulin receptor on the B cell surface or by a non-specific stimulus, e.g., a B cell mitogen such as lipopolysaccharide or pokeweed mitogen. Thus, a B cell can be a "virgin" B lymphocyte that has never previously been activated or a "memory" B lymphocyte that has previously been activated or the progeny of such a B lymphocyte.

As used herein, "antigenic" means capable of being recognized by an effector lymphocyte or an antibody molecule. Thus a substance is antigenic if it is recognized by an antigen specific receptor on, for example, a CTL, a Th, or a B lymphocyte producing antibody molecules or by an antibody molecule physically unassociated with a B lymphocyte.

An immunogen can be a polypeptide, carbohydrate, glycolipid, hapten or biomimetic thereof. A polypeptide immunogen, as defined above, can include without limitation, a compound of two or more subunit amino acids, amino acid analogs, or other peptidomimetics, regardless of post-translational modification, e.g. phosphorylation or glycosylation. The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

The amino acid sequence of the immunogens disclosed herein can be identical to the wild-type sequences of appropriate components. Alternatively, any of the components can contain mutations such as deletions, additions, or substitutions. All that is required is that the variant ligand have at least 5% (e.g., 10%, 20%, 30%, 40%, 50%, 60%, 70%, 80%, 90%, 95%, 99%, 100%, or even more) of the ability of the immunogen containing only wild-type sequences to induce an immune response against the naturally occurring wild-type immunogen. Substitutions will preferably be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

A polypeptide immunogen can include any peptide epitopes of a variety of lengths, for example, 7-50 (e.g. 7, 8, 9, 10, 11, 12, 13, 14, 15, 16, 17, 18, 19, 20, 21, 22, 23, 24, 25, 26, 27, 28, 29, 30, 32, 34, 36, 38, 40, 45, or 50) amino acid residues long. A polypeptide immunogen can include one or more epitopes, for example, 1, 2, 4, 6, 10, 20, 30, 50 or more.

Polypeptide immunogens can include one or more post-transcriptional modifications as described above in the Ligands section. An immunogen can be, without limitation, biotinylated, glycosylated, acetylated, alkylated, isoprenylated, lipoylated, or phosphorylated.

An immunogen can also be a molecule that is not a protein, e.g. a carbohydrate or glycolipid. Examples of carbohydrate and glycolipid immunogens, include, without limitation, bacterial lipopolysaccharide (LPS) or a fragment of it, microbial products bound by various Toll-like receptors (TLRs), bacterial diacyl and triacyl lipopeptides and lipoteichoic acid from bacteria, and zymosan from yeast cell walls.

The immunogen can be present in a killed or attenuated organism, in a crude cellular extract, a cell lysate or partially or substantially pure. The term "substantially pure" with respect to a naturally-occurring immunogen refers to an immunogen that has been separated from cellular components by which it is naturally accompanied, such that it is at least 60% (e.g., 70%, 80%, 90%, 95%, or 99%), by weight, free from naturally-occurring organic molecules with which it is naturally associated. Methods for purifying immunogens are known to those in the art. For example, in general, a substantially pure polypeptide will yield a single major band on a non-reducing polyacrylamide gel.

The immunogen can be a molecule expressed or released by any of a wide range of infectious agents, including, without limitation, viruses, viroids, bacteria, fungi, prions or parasites.

For example, viral pathogens can include, without limitation, influenza viruses, including the strain A (H1N5), hepatitis viruses (e.g, Hepatitis A, B, C and D), Arenaviruses, Bunyaviruses, Flaviviruses, Filoviruses, Alphaviruses, (e.g., Venezuelan equine encephalitis, eastern equine encephalitis, western equine encephalitis), Hantaviruses, human immunodeficiency viruses HIV1 and HIV2, feline immunodeficiency virus, simian immunodeficiency virus, measles virus, rabies virus, rotaviruses, papilloma virus, respiratory syncytial virus, Variola, and viral encephalitides, (e.g., West Nile Virus, LaCrosse, California encephalitis, VEE, EEE, WEE, Japanese Encephalitis Virus, Kyasanur Forest Virus). Bacterial pathogens can include, but are not limited to, *Bacillus anthracis, Yersinia pestis, Yersinia enterocolitica, Clostridium botu-*

*linum, Clostridium perfringens Francisella tularensis, Brucella* species, *Salmonella* spp., including *Salmonella enteriditis, Escherichia coli* including *E. coli* O157:H7, *Streptococcus pneumoniae, Staphylococcus aureus, Burkholderia mallei, Burkholderia pseudomallei, Chlamydia* spp., *Coxiella burnetii, Rickettsia prowazekii, Vibrio* spp., *Shigella* spp. *Listeria monocytogenes, Mycobacteria tuberculosis, M. leprae, Borrelia burgdorferi, Actinobacillus pleuropneumoniae, Helicobacter pylori, Neisseria meningitidis, Bordetella pertussis, Porphyromonas gingivalis*, and *Campylobacter jejuni.*

Fungal pathogens can include, without limitation, members of the genera Aspergillus, Penecillium, Stachybotrys, Trichoderma, mycoplasma, Histoplasma capsulatum, Cryptococcus neoformans, Chlamydia trachomatis, and *Candida albicans.*

Pathogenic protozoa can include, for example, members of the genera *Cryptosporidium*, e.g., *Cryptosporidium parvum, Giardia lamblia, Microsporidia* and *Toxoplasma*, e.g., *Toxoplasma brucei, Toxoplasma gondii, Entamoeba histolytica, Plasmodium falciparum, Leishmania major* and *Cyclospora cayatanensis.*

Examples of useful immunogens derived from pathogenic organisms include, for example, but are not limited to, influenza A M2 protein, hepatitis B surface antigen, HBV preS1 protein, HIV tat, HIV gp120, anthrax protective antigen, and botulinum toxin. An influenza M2 protein antigen can be the ectodomain peptide M2e, for example, SLLTEVETPIRNEWGCRCNDSSD (SEQ ID NO: 1), or a variant of the ectodomain peptide M2e, for example, SEQ ID NO: 3 or SEQ ID 4. An HBV preS1 protein can include the preS1 protein peptide 35-49, e.g., FGANSNNPDWDFNPNKDHWPEANQVGA (SEQ ID NO:2). Examples of useful non-peptidic immunogens include the pneumococcal polysaccharides from *Streptococcus pneumoniae.*

The immunogen can also be a molecule expressed by a mammal. For example, an immunogen can be a molecule whose expression is correlated with a particular disease state, for example, cancer or neurodegenerative disease.

Thus, the immunogen can be a tumor-associated antigen (TAA). As used herein, a TAA is a molecule (e.g., a polypeptide, carbohydrate or lipid) that is expressed by a tumor cell and either (a) differs qualitatively from its counterpart expressed in normal cells, or (b) is expressed at a higher level in tumor cells than in normal cells. Thus, a TAA can differ (e.g., by one or more amino acid residues where the molecule is a protein) from, or it can be identical to, its counterpart expressed in normal cells. Preferably it is not expressed by normal cells. Alternatively, it is expressed at a level at least two-fold higher (e.g., a two-fold, three-fold, five-fold, ten-fold, 20-fold, 40-fold, 100-fold, 500-fold, 1.000-fold, 5.000-fold, or 15.000-fold higher) in a tumor cell than in the tumor cell's normal counterpart. Examples of relevant cancers include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such ovarian cancer, vaginal cancer, bladder cancer, testicular cancer, prostate cancer or penile cancer, bone tumors, and vascular tumors. Relevant TAAs include, without limitation, carcinoembryonic antigen (CEA), RAGE, MART (melanoma antigen), MAGE (melanoma antigen) 1-4, 6 and 12, MUC (mucin) (e.g., MUC-1, MUC-2, etc.), tyrosinase, Pmel 17 (gp100), GnT-V intron V sequence (N-acetylglucoaminyltransferase V intron V sequence), Prostate cancer psm, PRAME (melanoma antigen), β-catenin, MUM-1-B (melanoma ubiquitous mutated gene product), GAGE (melanoma antigen)$_1$, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bc1-2, prostate specific antigen (PSA), and Ki-67.

Other immunogens that can be included in the immune conjugates disclosed herein are those derived from antigens that are involved in the initiation or progression of neurodegenerative diseases, e.g. Alzheimer's disease and Transmissible Spongiform Encephalopathies (TSEs), e.g., human prion diseases such as Creutzfeld-Jacob disease (CJD), variant CJD ("mad cow disease"), Gerstmann-Straussler-Scheinker syndrome (GSS); Fatal familial Insomnia (FFI); animal prion diseases such as Scrapic in sheep; bovine spongiform encephalopathy (BSE) in cows; transmissible mink encephalopathy (TME) in mink; chronic wasting disease (CWD) in elk and deer.

As used herein, a "neurodegenerative antigen" is a molecule (e.g., a polypeptide, carbohydrate or lipid) that is expressed by a neuronal cell in an individual with a neurodegenerative disease and either (a) differs qualitatively from its counterpart expressed in cells from an individual who does not have the neurodegenerative disease, e.g., the molecule appears in abnormal locations within the body or is associated with other molecules not normally found with the antigen in healthy individuals who do not have the neurodegenerative disease, or (b) is expressed at a higher level in cells from an individual who does not have the neurodegenerative disease. Thus, a neurodegenerative antigen can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart.

Examples of neurodegenerative antigens found in Alzheimer's disease include beta-amyloid, tau protein, alpha synuclein. Other neurodegenerative disease antigens can be derived from prions. As defined herein, a prion is small proteinaceous infectious particle that resists inactivation by procedures that modify nucleic acids. Prions are encoded by the prion-related protein gene (PrP). Mutant forms of the PrP protein aggregate as prions which can lead to fatal neurodegenerative disease. Thus, an immunogen can be a PrP polypeptide.

Germ cell immunogens can be useful in the generation of immune responses that block the function of germ cells, thereby interfering with conception. Germ cell antigens can include antigens on sperm cells. Examples include, without limitation sperm adhesion molecule 1 (SPAM-1), and human intra-acrosomal protein An immunogen can also be a non-toxic variant of a toxic substance (a "toxoid") that can be used to stimulate an immune response against the harmful form of the toxin. A toxoid can be, without limitation, a toxin that has been rendered less toxic or completely non-toxic through treatment with high temperature, aggregation, chemical reaction (e.g., formalin fixation), coupling to a carrier molecule, or molecular alteration (e.g., deletion, augmentation or substitution). A toxoid can be thus derived from a toxin such as, for example, ricin, anthrax or botulinum toxin types A, B, C, D, E, F or G.

An immunogen can also be a substance of abuse such as nicotine, or an opiate or opiate derivative. Such an immunogen can induce antibodies capable of binding and neutralizing the corresponding substance of abuse.

Forms of Immune Conjugates

The ligand and the immunogen are connected by a linker. A linker can be any reagent, molecule or macromolecule that connects the ligand and the immunogen such that a) the immune complex is stable under physiological conditions; b) the connection between the linker and the ligand does not alter the ability of the ligand to bind to its target on the surface of a circulating non-lymphoid cell; and c) the connection between the linker and the immunogen does not substantially affect the capacity of the immunogen to induce an effective immune response in a host against an infectious agent, cell or molecule on which the immunogen is naturally found.

Fusion proteins. A linker can be a peptide bond. That is, the ligand and the immunogen can be a fusion polypeptide comprising one or more amino acid segments from the ligand and one or more amino acid segments from the immunogen. The term “amino acid segment” as used herein refers to a contiguous stretch of amino acids within a polypeptide. For example, the amino acid residues 30 to 40 within a 100 amino acid polypeptide would be considered an amino acid segment. An amino acid segment can be a length greater than eight amino acid residues (e.g. greater than about nine, ten, 15, 20, 25, 30, 40, 50, 75, 100, 150, 200, 500, 1000, or more amino acid residues). In some embodiments, an amino acid segment can have a length less than 1000 amino acid residues (e.g., less than 500, less than 400, less than 350, less than 300, less than 200, or less than 100 amino acid residues). In other embodiments, an amino acid segment can have a length from about 20 to about 200 amino acid residues (e.g. about 30 to about 180 amino acid residues, or about 40 to about 150 amino acid residues).

The amino acid segments of the ligand can be contiguous with the amino acid segments of the immunogen or they can be separated by amino acids inserted as a structural spacer. A spacer segment can be one or more amino acids. The one or more amino acids can include amino acids that are the same or that are different. For example, a spacer can be a repeating series of a neutral amino acid (e.g., glycine, alanine, valine, isoleucine or lencine) ranging in number from 1 to 10 or more (e.g., 1, 2, 3, 4, 5, 6, 7, 9, 10 or more). Another example of a spacer configuration can be a series of interspersed amino acids that may be neutral (e.g. [glycine-alanine-glycine-alanine-glycine-alanine] (SEQ ID NO: 8) or [glycine-glycine-glycine-valine-valine-valine[ (SEQ ID NO: 9) or charged amino acids (e.g.,glutamate-glutamate -glutamate-arginine-arginine-arginine](SEQ ID NO: 10) or [aspartate-lysine-aspartate-lysine -aspartate-tysine]) (SEQ ID NO: 11) or amino acids with other functional groups (e.g., [proline-proline-proline-serine-serine-serine](SEQ ID NO: 12) orityrosine-glutamine-cysteine-methionine-tryptophan]) (SEQ NO: 13) ranging in number from 1 to 10 or more (e.g., 1, 2, 3, 4, 5, 6, 7, 8, 9, 20 or more). In another embodiment, a spacer configuration can be a sequence of amino acids derived from a naturally occurring protein such as the hinge region joining the heavy chain CH1 and CH2 domains of immunoglobulin G.

A fusion protein can be produced in vitro by continuous peptide synthesis according to standard chemical methods know to those in the art. Synthetic polypeptides can also be purchased from commercial sources.

A fusion protein can also be produced by recombinant DNA techniques. Nucleic acid segments encoding the ligand can be operably linked in the same open reading frame to nucleic acid sequences encoding the immunogen in a vector that includes the requisite regulatory elements, e.g., promoter sequences, transcription initiation sequences, and enhancer sequences, for expression in prokaryotic or eukaryotic cells. Methods well known to those skilled in the art can be used to construct expression vectors containing relevant coding sequences and appropriate transcriptional/translational control signals. Alternatively, suitable vector systems can be purchased from commercial sources.

Nucleic acid segments encoding ligands and immunogens are readily available in the public domain. Examples of nucleic acid segments encoding ligands include, without limitation, the erythrocyte (glycophorin A)-binding antigen of *Plasmodium falciparum* EBA-175 (Bharara et al., Mol. Biochem. Parasitol. 138: 123-9, 2004), or mouse anti-human glycophorin A monoclonal antibody heavy chain (GenBank accession # AAZ67132) and corresponding light chain (Genbank accession # AAA21366)). Examples of nucleic acid segments encoding immunogens include, without limitation, Hepatitis virus C polyprotein (Genbank public gi number 2654998); influenza virus A conserved M2 protein ectodomain peptide M2e (Genbank public gi number gi 78210829; HBV preS1 protein (Genbank public gi number gi 92111469).

The terms “nucleic acid” and “polynucleotide” are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. The nucleic acid molecules can be synthesized (for example, by phosphoramidite based synthesis) or obtained from a biological cell, such as the cell of a mammal. The nucleic acids can be those of mammal, e.g., humans, a non-human primates, cattle, horses, pigs, sheep, goats, deer, elk, dogs, cats, mustelids, rabbits, guinea pigs, hamsters, rats, or mice.

An “isolated” nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids disclosed herein also can be obtained by mutagenesis of, e.g. a naturally occurring DNA.

As used herein, the term "percent sequence identity" refers to the degree of identity between any given query sequence and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A query nucleic acid or amino acid sequence can be aligned to one or more subject nucleic acid or amino acid sequences using the computer program ClustalW (version 1.83, default parameters), which allows alignments of nucleic acid or protein sequences to be carried out across their entire length (global alignment). Chema et al., *Nucleic Acids Res.*, 31(13):3497-500 (2003). ClustalW can be run, for example, at the Baylor College of Medicine Search Launcher site (searchlauncher.bcm.tmc.edu/multi-Align/multi-align.html) and at the European Bioinformatics Institute site on the World Wide Web (ebi.ac.uk/clustalw).

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid.

A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

Vectors typically contain one or more regulatory regions. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

The vectors also can include, for example, origins of replication, scaffold attachment regions (SARs), and/or markers. A marker gene can confer a selectable phenotype, e.g., antibiotic resistance, on a cell. In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The expression vectors disclosed herein containing the above described coding can be used, for example, to transfect or transduce either prokaryotic (e.g., bacteria) cells or eukaryotic cells (e.g., yeast, insect, or mammalian) cells. Such cells can then be used, for example, for large or small scale in vitro production of the relevant fusion protein by methods known in the art. In essence, such methods involve culturing the cells under conditions which maximize production of the fusion protein and isolating the fusion protein from the cells or from the culture medium.

Conjugates. In another embodiment, the ligand and immunogen can be obtained separately, either through chemical synthesis or synthesis in vivo, purified and then linked non-covalently or covalently. A useful non-covalent linkage is a biotin-avidin linkage. The binding of biotin to avidin or streptavidin is essentially irreversible, with a reported Kd of $10^{-15}$M. The term "biotin-avidin linkage" as used herein refers to any linkage via biotin or a biotin derivative or biomimic (e.g., Strep-Tag (EBA, St. Louis, Mo.)) and avidin or an avidin derivative, streptavidin, or biotin-binding fragments or subunits of avidin or streptavidin.

Thus, the biotinylated ligand can be linked to a biotinylated immunogen via avidin or streptavidin, or biotin-binding fragments or subunits of avidin or streptavidin. Methods for forming biotin-avidin linkages are well known to those in the art. (See for example, Handbook of Affinity Chromatography, (Chromatographic Sciences Series, vol. 63) ed. T. Kline, ISBN: 0824789393—Marcel Dekker (1993). Avidin and avidin derivatives are available from commercial sources (Pierce Biotechnology, Rockford, Ill.; Invitrogen, Carlsbad, Calif.).

The ligand and the immunogen can also be linked through a biotin-streptavidin linkage that includes an additional biotinylated immunoglobulin. For example, a biotinylated ligand can be linked to an avidin molecule that is bound to a biotinylated antibody that specifically binds the immunogen.

Avidin and streptavidin have four biotin-binding sites each. By varying the relative ratios of the ligand and the immunogens used in the assembly of the targeted immune conjugates, it is possible to generate targeted immune conjugates with various ratios of linker: immunogen. Thus, biotin-avidin heterocomplexes can be prepared to include 1 molecule of the ligand and 3 molecules of the immunogen; 2 molecules each of ligand and immunogen; or 3 molecules of ligand and 1 molecule of immunogen. Assembly of the biotin-avidin linkages can be performed in any order. The composition of the assembled immune conjugates can be validated by SDS-PAGE and western blotting and LC/MS methods.

Alternative docking pairs of molecules with ultra-high affinity ($10^{-10}$M or more) may be used in place of biotin-avidin. An example of such a pair is vitamin B12 (cyanocobalamin), which is bound by vitamin B12-binding protein with a Kd of $10^{-10}$M).

The ligand and the immunogen can also be synthesized as separate entities (by either chemical synthetic or recombinant methods) and then linked together by standard chemical methods known in the art. Chemical cross-linking agents can be homo-bifunctional (the same chemical reaction takes place at each end of the linker) or hetero-bifunctional (different chemical reactions take place at the ends of the linker). The chemistries available for such linking reactions include, but are not limited to, reactivity with sulfhydryl, amino, carboxyl, diol, aldehyde, ketone, or other reactive groups using electrophilic or nucleophilic chemistries, as well as photochemical cross-linkers using alkyl or aromatic azido or carbonyl radicals. An example of a targeted conjugate coupled via a homobifunctional cross-linking reagent can be a complex of an anti-band 3 monoclonal antibody as the red blood cell-targeting component and anthrax protective antigen as the immunogen linked by disuccinimidyl suberate (DSS, Pierce, Rockford, Ill.). An example of a targeted conjugate coupled via a heterobifunctional cross-linking reagent can be an anti-glycophorin A monoclonal antibody as the targeting component and a non-toxic fragment of botulinum neurotoxin A as the immunogen linked by N-succinimidyl 3-[2-pyridyldithio]-propionamido (SPDP). In this example, the antibody is first derivatized at sulfhydryl groups with SPDP's pyridyldithio reactivity, followed by the addition of the toxin, whose amino residues react with SPDP's succinimidyl groups.

Examples of chemical cross-linking agents include, without limitation, glutaraldehyde, carbodiimides, bisdiazobenzidine, and N-maleimidobenzoyl-N-hydroxysuccinimide ester. Chemical cross-linkers are widely available from commercial sources (e.g., Pierce Biotechnology (Rockford, Ill.); Invitrogen (Carlsbad, Calif.); Sigma-Aldrich (St. Louis, Mo.); and US Biological (Swampscott, Mass.)).

In another embodiment, the ligand and the immunogen can be connected through a linking polymer. Examples of linking molecules include, but are not limited to linear or branched polymers or co-polymers (e.g. polyalkylene, poly(ethylene-lysine), polymethacrylate, polyamino acids, poly- or oligosaccharides, dendrimers). The ligand and the immunogen can be attached to the linking molecule or microparticle through a non-covalent high affinity linkage, e.g., streptavidin-biotin high affinity binding or chemical cross-linking techniques as described above.

For example, a polymer-supported targeted immunogen conjugate can be formed using a poly(ethylene-lysine) backbone. Such a linear copolymer backbone can be synthesized using bis(succinimidyl) poly(ethylene $glycol_{2000}$) (Fluka Chemicals) to react with the $\alpha$ and $\epsilon$ amino groups of lysine. The available carboxyl termini of the lysines can be activated using (1-ethyl-3-[3-dimethylaminopropyl]carbodiimide Hydrochloride) (EDC, Pierce Biotechnology) in preparation for coupling amine-containing compounds. The total length of the co-polymer can be determined, in part, by the duration of the polymerization reaction. The targeting and IMG units can be combined in various ratios since there are up to 10 positions in a 2000 dalton co-polymer built with, e.g., PEG units of 2,000 dalton. Co-polymers using shorter PEG units (e.g., 500 daltons) can also be synthesized.

One example of a polymer-based targeted immunogen conjugate can be the addition of equimolar amounts of a targeting monoclonal antibody (e.g. anti-CR2) and immunogen (e.g., influenza virus peptide M2e) to produce a complex with a co-polymeric scaffold studded with targeting antibody molecules as well as immunogen molecules.

In another embodiment, the ligand and the immunogen can be connected through a microparticle. Examples of linking microparticles include, but are not limited to, micelles, liposomes, fullerenes, nanotubes, or other colloidal complexes such as lipoproteins. Liposomes and micelles can be prepared by methods described in Lasic DD, 1998, TIBTech 16:307. Fullerenes and nanotubes can be purchased from American Dye Source (www.adsdyes.com). Lipoproteins can be purchased from Biodesign International (www.biodesign.com).

The ligand and the immunogen can be attached to the linking molecule or microparticle through a non-covalent high affinity linkage, e.g., avidin-biotin high affinity binding or chemical cross-linking techniques as described above. Alternatively or in addition, the ligand and/or the immunogen can be adsorbed or incorporated into a hydrophobic microparticle by hydrophobic affinity. A ligand and/or and immunogen with an available hydrophobic domain can spontaneously associate with a hydrophobic microparticle by hydrophobic partitioning. The hydrophobic domain on the ligand and/or immunogen can be a polyamino acid stretch comprised of repeating or mixed hydrophobic amino acids (e.g., poly-Ala, poly-Gly, poly-Leu, poly-Ile, or Ala-Gly-Leu-Ile (SEQ ID NO:5), etc.) or a bilayer-spanning polypeptide from a known trans-membrane protein, such as membrane IgM), alkyl chains (e.g., fatty acyl), or other hydrophobic structure (e.g., steroid). Such hydrophobic sequences can be naturally occurring sequences within the ligand and/or immunogen. Alternatively, such sequences can be introduced into the native amino acid sequence of the ligand or immunogen by standard recombinant DNA technology. The recombinant protein can be expressed and purified as described above.

The immune conjugates disclosed herein can include one or more of the same ligands or any combination of different ligands. The immune conjugate can also include one or more of the same immunogens or any combination of different immunogens. Thus, the immune conjugates can include immunogens that contain multiple copies (e.g., 2, 3, 4, 5, 6, 7, 8, 9, 10, 15, 10, 30, or more) of a single antigen or a single copy of multiple (e.g., 2, 3, 4, 5, 6, 7, 8, 9, 10, 15, 10, 30, or more) antigens or multiple copies (e.g., 2, 3, 4, 5, 6, 7, 8, 9, 10, 15, 10, 30, or more) of two or more antigens (e.g., 2, 3, 4, 5, 6, 7, 8, 9, 10, 15, 10, 30, or more). The immunogen can contain one or more copies of one or more peptide epitopes together with one or more copies of any of the non-peptide epitopes, e.g. post-transcriptional modifications, carbohydrates, or lipopolysaccharides.

Further, a targeted immune conjugate can include an immunogen that includes more than one polypeptide, or any combination of different polypeptides. It is noted that each polypeptide in a composition can have an identical amino acid sequence. In addition, the polypeptides in a composition can contain different amino acid segments, each of which can act as a defined immunogenic unit against which an immune response is desired. Thus, the polypeptides in a composition can contain different amino acid segments that correspond to any region from a polypeptide including, without limitation, receptor binding regions, ligand binding regions, enzyme active sites, enzyme cleavage sites of polypeptide substrates, antigen-binding regions of antibodies, and epitopes recognized by antibodies. Typically, the administration of a polypeptide results in the formation of antibodies having specificity for an epitope or combination of epitopes formed by the amino acid segments within one or more of the polypeptides in the composition.

III. Methods of Use

The immune conjugates disclosed herein are generally useful for generating immune responses and as prophylactic vaccines or immune response-stimulating therapeutics. As used herein, "prophylaxis" can mean complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease.

The methods disclosed herein can be applied to a wide range of species, e.g., humans, non-human primates (e.g., monkeys), horses, cattle, pigs, sheep, deer, elk, goats, dogs, cats, mustelids, rabbits, guinea pigs, hamsters, rats, and mice. Thus, they can be used, for example, as vaccines or therapeutic agents against infectious diseases, including diseases that can potentially result from bioterrorism attacks. The immune conjugates can be used in the preparation of a medicament for treatment of an infectious disease. Infectious diseases can include diseases caused by any of the pathogens listed herein. Examples include, without limitation, influenza, HIV-AIDS, hepatitis, botulism, plague, smallpox, tularemia, viral hemorrhagic fevers, brucellosis, gastrointestinal disease induced by pathogenic forms of *E. coli, Salmonella* and *Shigella*, glanders, melioidosis, psittacosis, Q fever, Staph infection, typhus fever, viral encephalitis, water and foodborne safety threats, cholera, diphtheria, endocarditis, Legionaire's disease, Listeriosis, periodontal disease, Asperigillosis, Blastomycosis, histoplasmosius, trypanosomiasis, malaria, Giardiasis, Schistosomiasis, toxoplasmosis, smallpox, west Nile virus.

In addition, the immune conjugates can be useful as both prophylactics and therapeutics for cancer (e.g., any of those recited above). The immune conjugates can be employed to stimulate an immune response against cells in a cancer patient or can be administered in cases where a subject is at relatively high risk for a cancer (e.g., lung cancer in a tobacco smoker or melanoma in a subject with multiple nevi). Moreover, as described above, the immune conjugates can also be useful in therapy or prophylaxis of neurodegenerative diseases. Thus the immune conjugates can be administered to an individual with Alzheimer's disease or TSE or administered to an individual who is at risk for developing Alzheimer's disease or TSE.

Immune conjugates disclosed herein can also be useful as a contraceptive vaccine, when the immunogen is a germ cell antigen.

The immune conjugates disclosed herein can also be useful as prophylactics and therapeutics against medical conditions that result from exposure to toxins. Such targeted immune conjugates that include non-toxic variants of toxic substances, e.g., ricin, botulinum toxin, nicotine and other drugs, can be used to stimulate an immune response against the harmful form of the toxin, and thus protect against or mitigate the potential damage the toxin or drug may cause.

The immune conjugates can be administered directly to a mammal. The immune conjugates can be used in the preparation of a medicament. Generally, the immune conjugates can be suspended in a pharmaceutically-acceptable carrier (e.g., physiological saline). A composition can be made by combining any of the immune conjugates provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters, for example. Aqueous carriers include, without limitation, water, alcohol, saline, and buffered solutions. Preservatives, flavorings, and other additives such as, for example, antimicrobials, anti-oxidants, chelating agents, inert gases, and the like also may be present. It will be appreciated that any material described herein that is to be administered to a mammal can contain one or more pharmaceutically acceptable carriers.

Any composition described herein can be administered to any part of the host's body. A composition can be delivered to, without limitation, the joints, nasal mucosa, blood, lungs, intestines, muscle tissues, skin, or peritoneal cavity of a mammal. In addition, a composition can be administered by intravenous, intraperitoneal, intramuscular, subcutaneous, intramuscular, intrarectal, intravaginal, intrathecal, intratracheal, intradermal, or transdermal injection, by oral or nasal administration, by inhalation, or by gradual perfusion over time. In a further example, an aerosol preparation of a composition can be given to a host by inhalation.

The dosage required depends on the route of administration, the nature of the formulation, the nature of the patient's illness, the subject's size, weight, surface area, age, and sex, other drugs being administered, and the judgment of the attending physician. Suitable dosages are in the range of 0.01-1,000 μg/kg. Wide variations in the needed dosage are to be expected in view of the variety of immune conjugates available and the differing efficiencies of various routes of administration. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the immune conjugate in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, an immune conjugate can be administered once a month for three months or once a year for a period of ten years. It is also noted that the frequency of treatment can be variable. For example, an immune conjugate can be administered once (or twice, three times, etc.) daily, weekly, monthly, or yearly.

Alternatively or in addition the immune conjugates can be administered along with an adjuvant. An "adjuvant" is an immunological compound that can enhance an immune response against a particular antigen such as a polypeptide. Examples of adjuvants include alum and other aluminum-based compounds (e.g., $Al_2O_3$). Aluminum-based compounds can be obtained from various commercial suppliers. Other adjuvants include immuno-stimulating complexes (ISCOMs) that can contain such components as cholesterol and saponins; one or more additional immunostimulatory components, including, without limitation, muramyldipeptide (e.g. N-acetylmuramyl-L-alanyl-D-isoglutamine; MDP), monophosphoryl-lipid A (MPL), and formyl-methionine containing tripeptides such as N-formyl-Met-Leu-Phe. Such compounds are commercially available from Sigma Chemical Co. (St. Louis, Mo.), for example. Other adjuvants can include CpG oligodeoxynucleotides (Coley Pharmaceuticals), QS21 (Cambridge Biotech) and MF59 (Chiron).

The compositions provided herein can contain any ratio of adjuvant to immune conjugate. The adjuvant:immune conjugate ratio can be 50:50 (vol:vol), for example. Alternatively, the adjuvant:immune conjugate ratio can be, without limitation, 90:10, 80:20, 70:30, 64:36, 60:40, 55:45, 40:60, 30:70, 20:80, or 90:10.

An effective amount of any composition provided herein can be administered to a host. The term "effective" as used herein refers to any amount that induces a desired immune response while not inducing significant toxicity in the host. Such an amount can be determined by assessing a host's immune response after administration of a known amount of a particular composition. In addition, the level of toxicity, if any, can be determined by assessing a host's clinical symptoms before and after administering a known amount of a particular composition. It is noted that the effective amount of a particular composition administered to a host can be adjusted according to a desired outcome as well as the host's response and level of toxicity. Significant toxicity can vary for each particular host and depends on multiple factors including, without limitation, the host's disease state, age, and tolerance to pain.

Any method can be used to determine if a particular immune response is induced. For example, antibody responses against a particular immunogen can be determined using an immunological assay (e.g. ELISA or lymphocyte proliferation assay). In such an assay, the wells of a microtiter plate can be coated with the immunogen and incubated with serum from a mammal treated with the immune conjugate designed to produce antibodies against the corresponding immunogen in that mammal, and the presence or absence of antibodies against the immunogen can be determined by standard methods know to those in the art. In addition, clinical methods that can assess the degree of a particular disease state can be used to determine if a desired immune response is induced. For example, in a cancer patient, a reduction in tumor burden can indicate a desired immune response in a patient treated with a composition designed to stimulate an immune response against a tumor antigen expressed on the patient's tumor.

Alternatively, a polynucleotide containing a nucleic acid sequence encoding an immune conjugate of interest can be delivered to an appropriate cell of the animal. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the fusion protein of interest with an initiator methionine and optionally a targeting sequence is operatively linked to a promoter or enhancer-promoter combination. Promoters and enhancers are described above.

Polynucleotides can be administered in a pharmaceutically acceptable carrier. Pharmaceutically acceptable carriers are biologically compatible vehicles which are suitable for administration to a human or other mammalian subject, e.g., physiological saline. A therapeutically effective amount is an amount of the polynucleotide which is capable of producing a medically desirable result (e.g., a T cell response) in a treated mammal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

The immune conjugates provided herein can be administered in conjunction with other therapeutic modalities to an individual in need of therapy. The immune conjugates can be given prior to, simultaneously with or after treatment with other agents. In the case of infectious disease, the immune conjugates can be administered in conjunction with any antimicrobial agent, e.g. an antibiotic, e.g. including, without limitation, aminoglycosides, cephalosporins, macrolides, penicillins, peptides, quinolones, sulfonamides, tetracyclines; an antiviral, including without limitation, amantadine, rimantadine, zanamavir and oseltamivir; an anti-fungal, including, without limitation, echinocandin, caspofungin, anidulafungin; or anti-parasitic agent, including, without limitation, chlorquine, mebendazole, and clotrimazole.

The immune conjugates can also be used in conjuction with standard anti-cancer therapies, including, without limitation, chemotherapy, e.g., alkylating agents, anthracyclines, cycloskeletal disruptors, topoisomerase inhibitors, nucleotide analogues, platinum-based agents, retinoids, vinca alkaloids; radiation therapy, hormone ablation and surgery. The immune conjugates can also be used in conjunction with other therapeutics for neurodegenerative diseases, including donepezil, galantamine, memantine.

In vitro application of the immune conjugates can be useful, for example, in basic scientific studies of immune mechanisms or for production of activated T cells for use in either studies on T cell function or, for example, passive immunotherapy.

Articles of Manufacture

Also disclosed are articles of manufacture that can include immune conjugates as provided herein. Components and methods for producing articles of manufacture are well known. An article of manufacture can include, for example, one or more immune conjugates. In addition, an article of manufacture further may include, for example, packaging materials, instructions for use, buffers or other control reagents for treating or monitoring the condition for which prophylaxis or treatment is required.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Assembly of Tripartite Conjugates of the Biotinylated Monoclonal Antibody Anti-TER-119, Streptavidin and the Biotinylated Peptide M2E Conjugates to deliver the immunogen M2e, to the mouse red blood cell (mRBC), were prepared by coupling the peptide with the rat anti-mouse monoclonal antibody anti-TER-119 and using streptavidin (StAv) as the linker.

Preparation of tripartite immune conjugates. The peptide M2e (SLLTEVETPIRNEWGCRCNDSSD) (SEQ ID NO: 1) was produced by peptide synthesis (BioWorld, Dublin Ohio) to contain a biotinylated lysine residue at its carboxy terminus. Anti-TER-119, a rat anti-mouse IgG2b,κ monoclonal antibody, was purchased biotinylated from BD-Pharmingen, as was the isotype control, biotinylated rat IgG2b,κ. The extent of biotinylation of these products was not available from the manufacturer. Streptavidin was purchased from Sigma-Aldrich.

Biotinylated M2e peptide (b-M2e) (SEQ ID NO: 1) was incubated with StAv in phosphate-buffered saline, 10 mM sodium phosphate, 140 mM NaCl, pH 7.4 (PBS) at ambient temperature at various molar ratios. After 30 min incubation biotinylated anti-TER-119 antibody (b-Ab) was added and the incubation was continued for an additional 30 min with occasional agitation. Reaction samples were analyzed by 3 to 8% gradient gel electrophoresis under native (or non-denaturing) conditions (NDGE, Invitrogen, tris-glycine running buffer) and visualized by Coomassie blue staining. The results showed that mixtures of conjugates of different apparent molecular weights and stoichiometries were formed caused by differential cross-linking by StAv between the biotinylated peptide and the Ab. The relative amounts of reagents used in the reactions are shown in the grids below the respective NDGE images.

Characterization of tripartite immune conjugates. In the experiment depicted in FIG. 1 the amounts of StAv and b-Ab were kept constant but the amount of b-M2e was varied as indicated. Pre-incubation of 100 or 200 μmol b-M2e with 20 pmol StAv, which is well in excess of the 80 pmol required to saturate the StAv biotin-binding sites, resulted in formation of StAv(M2c)$_4$. This conjugate migrated faster than free StAv and similarly to unreacted b-M2e (lanes 10-12 compared to lane 3).

Because the mobility of reagents in NDGE is not solely determined by their molecular weight but also by their conformation and charge, StAv migrated considerably faster than Ab, to a location on the gel that was slightly above the peptide b-M2e. Addition of b-M2e peptide to StAv, while increasing its MW, caused a shift in the complex's migration downward, to the position of unreacted b-M2e (lanes 3 and 6). That this was the effect of binding of b-M2e to StAv was demonstrated by the reaction in lane 4, in which excess non-biotinylated peptide M2e did not alter the mobility of StAv). When b-M2e+StAv mixtures containing an excess of b-M2e were combined with b-Ab there was no shift in the migration of the Ab (lanes 11 and 12, compared to lane 5).

The admixture of 50 pmol or less b-M2e, which was below the theoretical 80 pmol needed to saturate 20 pmol StAv, did shift the mobility of the added b-Ab upward indicating the presence of Ab-StAv$_n$, where n represents the number of biotin residues per Ab molecule. In addition, the laddering pattern in lanes 7-10, indicated the presence of possible higher order complexes such as Ab-StAv-Ab, Ab-StAv2-Ab2, Ab-StAv-Ab-StAv-Ab, etc. Useful tripartite complexes were those that did not include unreacted Ab; these complexes had a mobility that was shifted upward from that of the unconjugated antibody, but not to a degree that prevented the complexes from entering the gel, e.g., in lanes 9-10, where the ratio of tetravalent StAv:b-M2e was approximately 1:3.

Figure 2:
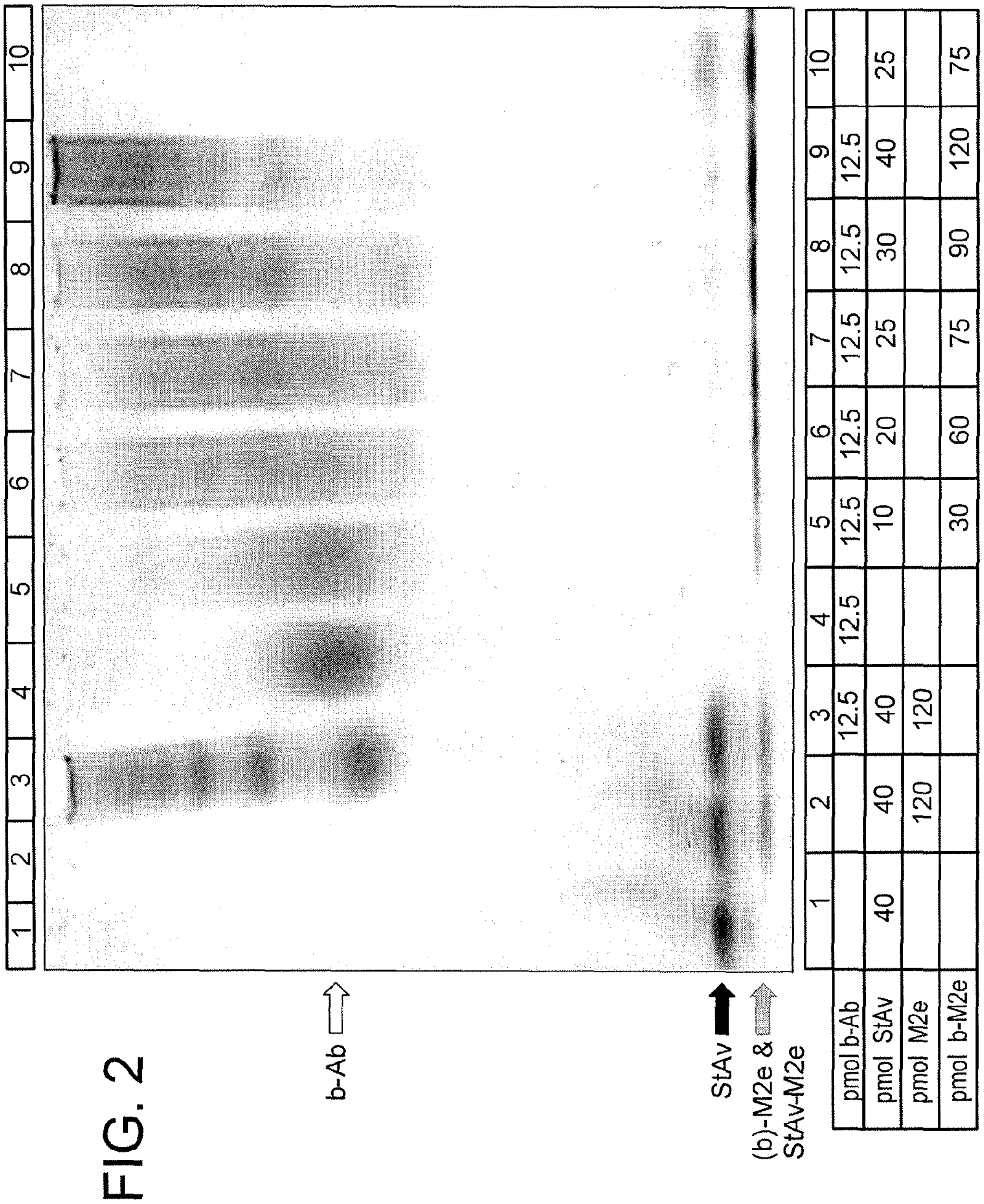
FIG. 2 depicts the electrophoretic mobility of tripartite immune conjugates containing biotinylated antibody and a constant ratio of streptavidin, and biotinylated M2e peptide (SEQ ID NO:1).

Conditions for the formation of the Ab-StAv-M2e tripartite immune conjugates were analyzed in the experiment shown in FIG. 2. The concentration of b-Ab was held constant at 12.5 pmol, and different amounts of StAv-b-M2e conjugates preformed at a 1:3 ratio were added. Complexes of various stoichiometries were seen in all combinations, with the higher order complexes seen where StAv was in excess over b-Ab (lanes 6-9). FIG. 2 also showed that in the 1:3 StAv:b-M2e mixtures there were some StAv molecules that had a minimum of 2 free biotin-binding sites which were responsible for cross-linking b-Ab molecules (lanes 5-9). This experiment also indicated that the antibody molecules contained more than one biotin residue. If b-Ab were mono-biotinylated, the reaction with free StAv would lead to a preponderance of Ab tetramers, with lesser amounts of trimers, dimmers and monomers. Lane 3 shows that this is not the case. Instead there were more types of complexes without apparent preponderance of tetramers.

One objective of these experiments was to define conditions that produced tripartite conjugates with a maximum number of M2e peptides per Ab molecule. The stoichiometric ratios of Ab:StAv:M2e in the experiments described above are listed in Table 1.

TABLE 1

Molar ratios of the components in tripartite conjugate reactions depicted in FIGS. 1 and 2 (normalized to the concentration of Ab).

| | FIG. 1 | | | | | FIG. 2 | | | | |
|---|---|---|---|---|---|---|---|---|---|---|
| lane | 8 | 9 | 10 | 11 | 12 | 5 | 6 | 7 | 8 | 9 |
| Ab | 1.0 | 1.0 | 1.0 | 1.0 | 1.0 | 1.0 | 1.0 | 1.0 | 1.0 | 1.0 |
| StAv | 1.3 | 1.3 | 1.3 | 1.3 | 1.3 | 0.8 | 1.6 | 2.0 | 2.4 | 3.2 |
| M2e | 0.7 | 1.7 | 3.3 | 6.7 | 13.3 | 2.4 | 5.4 | 6.0 | 7.2 | 9.6 |

The conditions in which most of the Ab was shifted by the reaction, but the complexes formed were not too large to diffuse into the gel are found in FIG. 1, lanes 9 and 10 and FIG. 2, lanes 6, 7 and 8. The immune conjugates that included the highest proportion of peptides per Ab (6 or 7.2) were those shown in lane 7 or 8 of FIG. 2.

Example 2

Analysis of Anti M2e Activity in Mice Challenged with the Immune Conjugate Biotinylated Rat Anti-Mouse TER-119 Mab–Streptavidin-Biotinylated M2e Peptide Mice are challenged intraperitoneally with an immune conjugate of biotinylated rat anti-mouse TER-119 Mab–streptavidin-biotinylated M2e peptide ((SEQ ID NO: 1)) and their serum antibody response to M2e (SEQ ID NO: 1) is assayed.

M2e peptide (SEQ ID NO: 1) with a C-terminal addition of lysyl-ϵ-N-biotin or PGGG (SEQ ID NO:6) is synthesized by solid phase peptide synthesis (R10-World). This peptide is coupled to streptavidin (StAv) (Sigma-Aldrich) at a peptide: StAv molar ratio of 3:1 by mixing with b-Ab, as described in Example 1. Identical tripartite conjugate is prepared using biotinylated rat IgG (BD Pharmingen) as a control. To prepare TER-119-StAv and rat IgG-StAv conjugates the StAv is first reacted at a biotin:StAv molar ratio of 3:1 to occupy 3 of the 4 biotin-binding sites (BBSs) on each StAv molecule. In groups receiving uncoupled StAv, it is first reacted with a minimum of 4 molar equivalents of biotin to saturate all the BBSs. M2e peptide conjugated to keyhole limpet hemocyanin (KLH) is produced by Bio-World.

Groups of 5 mice each (Balb/C, female, 6-8 weeks old) are injected intravenously (i.v.) in the tail vein with a range of free and conjugated peptide doses (0.01 to 10 μg equivalent of peptide in 50 μl PBS). Since StAv and TER-119 (a rat IgG) are also immunogenic in mice, Ab titers against them alone or in RBC-targeted conjugates are also evaluated. Groups 1-6 are the minimum set to analyze the relative anti-M2e responses. Groups 7-15 include additional controls to further analyze the anti-StAv and anti-rat IgG responses, as well as the effect of simply mixing the various components, instead of coupling them into targeted conjugates. The experimental design is depicted in the table below:

TABLE 2

Experimental design: Example 2.

| Group number | Ligand | Linker | Immunogen |
|---|---|---|---|
| 1 | Biotinylated Anti-TER119 | streptavidin | Biotinylated M2e |
| 2 | Biotinylated Rat IgG | streptavidin | Biotinylated M2e |
| 3 | — | streptavidin | Biotinylated M2e |
| 4 | KLH | Chemical conjugate | M2e |
| 5 | — | — | M2e |
| 6 (PBS injected only) | — | — | — |
| 7 | Biotinylated Anti-TER119 | streptavidin | — |
| 8 | Biotinylated Rat IgG | streptavidin | — |
| 9 | Biotinylated Anti-TER119 | streptavidin | M2e |
| 10 | Biotinylated Rat IgG | streptavidin | M2e |
| 11 | — | streptavidin | M2e |
| 12 | Biotinylated Anti-TER119 | — | M2e |
| 13 | Biotinylated Rat IgG | — | M2e |
| 14 | Biotinylated Anti-TER119 | — | — |
| 15 | Biotinylated Rat IgG | — | — |

The mice are boosted with a repeat i.v. injection after 2 and again after 4 weeks. Blood samples (~100 μl) are collected retro-orbitally prior to and every week after the primary injection for 5 weeks. Blood samples are chilled on ice and allowed to clot overnight. The tubes are centrifuged and serum is collected and stored at −20° C.

Mouse IgG titers against all 3 antigens (Ags), M2e, StAv and rat IgG, are determined by ELISA. ELISA plates (Immulon, VWR) are coated with 100 μl Ag at 10 μg/ml in sodium carbonate ($Na_2CO_3$) buffer, 50 mM, pH 9.6 overnight at 4° C. Plates are washed and blocked with 200 μl/well of 3% BSA in PBS containing 0.05% Tween-20 (PBST) for 1.5 hours at room temperature (RT). Wash 3× with 200 μl/well of PBST. Dispense 100 μl/well of individual mouse sera at 1:50 dilution in PBST in duplicates and prepare serial dilutions in 1:3 X increments. Allow mouse antisera to bind for 1.5 hours at RT and wash the plates as above. Add 100 μl/well goat anti-mouse IgG conjugated with horseradish peroxidase (diluted per vendor instructions, Sigma), incubate for 1 hour at RT, and wash as above. Add 100 μl/well substrate (SureBlue, KPL) and read absorbance at 405 nm. Positive control Abs are: Mouse Mab 14C2 which recognizes the N-terminal ectodomain epitope of M2 (Abeam), mouse Mab anti-StAv (Abeam) and mouse polyclonal anti-rat IgG (H & L chains) (Invitrogen).

Example 3

Analysis of Anti M2e Activity in Mice Challenged with the Immune Conjugate Biotinylated Rat Anti-Mouse TER-119 Mab–Streptavidin-Biotinylated M2e Peptide (SEQ ID NO: 1): Comparison of Different Routes of Administration The effect of the route of administration on the serum antibody response to M2e peptide in mice challenged with an immune conjugate of biotinylated rat anti-mouse TER-119 Mab+streptavidin-biotinylated M2e peptide is evaluated by comparing serum titers of anti-M2e antibodies in mice immunized intraperitoneally, intravenously, subcutaneously and intramuscularly. The full Mab-StAv-IMG conjugate is compared to the non-targeted StAv-IMG partial complex, as well as to PBS vehicle. The dose will be 1.0 μg equivalent of M2e peptide (SEQ ID NO: 1). Immunizations and ELISA analysis are performed as described in Example 2.

Example 4

Analysis of Anti-M2e Fecal IgG and IgA Activity in Mice Challenged with the Immune Conjugate Biotinylated Rat Anti-Mouse TER-119 Mab–Streptavidin-Biotinylated M2e Peptide (SEQ ID NO: 1)

Mice are dosed with TER-119–StAv–M2e conjugate and controls as depicted in Table 2 and following the dosing schedule in Example 2:

TABLE 3

Experimental design: Example 4.

| Group number | Ligand | Linker | Immunogen |
|---|---|---|---|
| 1 | Biotinylated Anti-TER119 | streptavidin | Biotinylated M2e |
| 2 | Biotinylated Rat IgG | streptavidin | Biotinylated M2e |
| 3 | — | streptavidin | Biotinylated M2e |
| 4 | KLH | Chemical conjugate | M2e |
| 5 | — | — | M2e |
| 6 (PBS injected only) | — | — | — |

Feces are collected at the times described in Example 2. Soybean trypsin inhibitor (0.1 mg/ml in PBS) is added to every 0.1 g of feces, which are vortexed in a mini-beadbeater (Biospec Products) for 10 sec at 2500 rpm, and debris is removed by centrifugation at 9000×g at 4° C. for 15 min. The supernatant is assayed for anti-M2e IgG titer in the ELISA set-up described in Example 2, but also for IgA by adding anti-IgA $2^{nd}$ antibody (goat anti-mouse IgA conjugated with horseradish peroxidase (Sigma-Aldrich).

Example 5

Analysis of Anti-M2e Activity in Mice Challenged with the Immune Conjugate Biotinylated Rat Anti-Mouse CD21/CD35 Mab–Streptavidin-Biotinylated M2e Peptide (SEQ ID No: 1)

Mice are injected with an immune conjugate of biotinylated rat anti-mouse CD21/CD35 Mab+streptavidin-biotinylated M2e peptide (influenza) and their serum antibody response to M2e is assayed. The anti-CD21/CD35 antibody is purchased from eBioscience. The conjugate is prepared according to the method described in Example 2. Groups of 5 mice each (Balb/C, female, 6-8 weeks old) are injected intravenously (i.v.) with a range of free and conjugated peptide doses (0.01 to 10 μg equivalent of peptide in 50 μl PBS) according to the experimental design in shown in Table 4 below.

TABLE 4

Experimental design: Example 5.

| Group number | Ligand | Linker | Immunogen |
|---|---|---|---|
| 1 | Biotinylated Anti-CD21/CD35 | streptavidin | Biotinylated M2e |
| 2 | Biotinylated Rat IgG | streptavidin | Biotinylated M2e |
| 3 | — | streptavidin | Biotinylated M2e |
| 4 | KLH | Chemical conjugate | M2e |
| 5 | — | — | M2e |
| 6 (PBS injected only) | — | — | — |
| 7 | Biotinylated Anti-CD21/CD35 | streptavidin | — |
| 8 | Biotinylated Rat IgG | streptavidin | — |
| 9 | Biotinylated Anti-CD21/CD35 | streptavidin | M2e |
| 10 | Biotinylated Rat IgG | streptavidin | M2e |
| 11 | — | streptavidin | M2e |
| 12 | Biotinylated Anti-CD21/CD35 | — | M2e |
| 13 | Biotinylated Rat IgG | — | M2e |
| 14 | Biotinylated Anti-CD21/CD35 | — | — |
| 15 | Biotinylated Rat IgG | — | — |

Immunizations and ELISA analysis will be performed as described in Example 2.

Example 6

Analysis of Anti-M2C Activity in Mice Challenged with the Immune Conjugate Biotinylated *Plasmodium falciparum* EBA-175 Peptide 1085-1096 (SEQ ID No: 7) (pEBA)+Streptavidin-Biotinylated M2e Peptide Since *Plasmodium falciparum* EBA-175 peptide 1085-1096 binds human, but not mouse RBCs, the mouse experiments are performed in human GphA-transgenic mice (see Auffrey, et al., 2001, Blood 97:2872-2878. Glycophorin A dimerization and band 3 interaction during erythroid membrane biogenesis: in vivo studies in human glycophorin A transgenic mice). Alternately, the corresponding binding protein derived from other species of *Plasmodium*, e.g., *P. bergheii* or *P. yoelii yoelii*, which bind mouse RBCs is used (referred to as $pEBA_m$). Complexes are assembled and immunizations and ELISA analysis are performed as described in Example 2.

Example 7

Analysis of Anti-M2e Activity in Mice Challenged with the Synthetic Peptide pEBA-Glycine-Glycine-Glycine-M2e Peptide Mice are injected intravenously with a synthetic peptide of the sequence $pEBA_m$-175 SEQ ID NO: 7 linked via three glycine residues to the M2e peptide (SEQ ID NO: 1) described in Example 1 above and according to the scheme depicted in Table 5. Each mouse receives a range of free and conjugated peptide doses (0.01 to 10 μg equivalent of M2e peptide in 50 μl PBS) intravenously and blood samples are collected and analyzed according to the schedule in Example 2.

TABLE 5

| Experimental Design: Example 7. | | | |
|---|---|---|---|
| Group number | Ligand | Linker | immunogen |
| 1 | pEBA$_m$ | Gly-Gly-Gly | M2e |
| 2 | pEBA$_m$ (scrambled) | Gly-Gly-Gly | M2e |
| 3 | KLH | Chemical conjugate | M2e |
| 4 | — | — | M2e |
| 5 (PBS injected only) | — | — | — |

Example 8

Analysis of Anti-HBV Peptide (preS1 Amino Acids 34-59 (SEQ ID NO:2), or pHBV) Activity in Mice Challenged with the Immune Conjugate Biotinylated Rat Anti-Mouse TER-119 Mab+Streptavidin-Biotinylated pHBV Mice are challenged with immune conjugates in which the immunogen is an HBV (hepatitis B virus) peptide preS1 amino acids 34-59 (Hu W G, et al. 2005. World J Gastroenterol. 11:2088-2094. Identification of the immunogenic domains in HBsAg preS1 region using overlapping preS1 fragment fusion proteins) or pHBV coupled to biotinylated TER-119 Mab. Experimental groups, immunizations and ELISA analysis are as described in Example 2.

Example 9

Analysis of Anti-M2e Activity in Mice Challenged with the Immune Conjugate Biotinylated Mouse Anti-Mouse Band 3 Mab–Streptavidin-Biotinylated M2e Peptide (SEQ ID NO:1)

Mouse anti-mouse band 3 Mabs have been produced in several labs from NZB mice. The immune conjugate, biotinylated mouse anti-mouse band 3 Mab–streptavidin-biotinylated M2e peptide, is produced according to the method in Example 1 with an IgG anti-mouse band-3 Mabs (e.g., 34-3C or class-switched 4C8 (Fossati-Jimack, 2002, J Autoimmun 18:17-25. Selective increase of autoimmune epitope expression on aged erythrocytes in mice: implications in anti-erythrocyte autoimmune responses.)), and is evaluated according to the protocol in Example 2.

Example 10

Optimization of the Degree of Biotinylation of the Targeting Mabs

Establish the optimal number of StAv-IMG units to couple to the biotinylated Mab. Maximize IMG load while retaining full target binding capacity of the Mab.

The FluoReporter Biotin Quantitation Kit (Invitrogen) is used for estimating the molar ratio of biotin:protein. Mab anti-TER-119 is biotinylated using amino-reactive (Pierce EZ-link NHS biotin) and carbohydrate-reactive (Pierce EZ-link hydrazide-biotin) reagents at various levels by adding a range of biotinylation molar excess factors (e.g., 3×, 5×, 10×, 50×, 250×). Add a 5× molar excess StAv per mole of biotinylated Mab to saturate all biotinylated sites. Test functional integrity of the biotinylated Mab preparations by binding to mouse RBCs. Use goat anti-rat IgG conjugated with fluorescence isothiocyanate (FITC) to detect RBC-bound TER-119 using flow cytometry. Select the condition that results in the highest degree of biotinylation of the TER-119 Mab while retaining maximum RBC-binding. Use un-biotinylated TER-119 Mab and goat anti-rat IgG-FITC as the reference.

Example 11

Determination of the Optimal Stoichiometry of Mab–StAv-IMG

The effect of loading 1, 2 or 3 IMGs per StAv and the effect of binding 1 or more of these StAv-IMG conjugates per targeting Mab is compared. The optimal construct is identified based on the elicited response in vivo (see Example 2). Prepare anti-TER-119+StAv+M2e conjugates at various ratios (e.g., 1:1:1, 1:1:3, 1:2:2, 1:2:6, 1:3:3, 1:3:9) and administer them to mice as in Example 2 (always administer 1.0 μg equivalent of M2e). Compare the resulting anti-M2e titers.

Example 12

Comparison of Monovalent, Divalent and Trivalent Peptide-Mediated Targeting of IMG to RBC Biotinylated pEBA$_m$ (SEQ ID NO:7) (see Example 7) is used as the targeting ligand and biotinylated M2e is used as the IMG. The following constructs are prepared: 1pEBA$_m$:1 StAv:3M2e, 2pEBA$_m$:1 StAv:2M2e and 3pEBA$_m$:1StAv:1M2e. Inject mice with each of the constructs containing equal equivalents of M2e (1.0 μg). Evaluate the elicited immune response according to the methods in Example 2.

Example 13

Evaluation of the Efficacy of Immunizing with a Construct in which the Targeting Component and the IMG are Covalently Bound to a Common Polymer Backbone Synthesize each component peptide (e.g., pEBA$_m$ (SEQ ID NO:7) and M2e (SEQ ID NO: 1)) with an added Lys whose α-carboxyl group is joined to the peptide's C-terminus, leaving the α and ϵ amino groups of Lys free. Co-polymerize various ratios of the components with bis-succinimidyl poly (ethylene glycol), or BS-PEG (mean molecular weight 2,000 da). The free a and a amino groups of Lys are linked to the reactive PEG units to create a co-polymer that has the pattern PEG-P-PEG-P-PEG-P-PEG . . . , where P is either peptide pEBA$_m$ or M2e in a random distribution. The ratio of pEBA$_m$ to M2e is a function of the ratio of added peptides to the polymerization reaction. Prepare co-polymer backbone targeted IMG constructs in which the Mab:IMG ratios are 0:10 (un-targeted multivalent IMG control), 1:9, 3:7, 5:5, 7:3 and 9:1. Evaluate their efficacy by injecting 1.0 μg equivalents of M2e as described in Example 2.

Example 14

Preparing Targeted Constructs Using a Microparticulate Linking Component

Liposomes containing a biotinylated lipid in the bilayer (e.g., phosphatidyl ethanolamine reacted with succinimidyl-biotin) are prepared. The exposed biotin groups are used to bind StAv and then the StAv's biotin-binding sites are loaded with biotinylated targeting and IMG components at various ratios. The comparatively large liposomal surface permits adding many more units of each component without causing steric hindrance. In order to prevent StAv from cross-linking the exposed biotin groups on the liposomal surface, pre-load 3 mole equivalents of either targeting or IMG units (or combinations of these) per mole of StAv, and then add this conjugate to the liposomes. Administer and analyze as in Example 2.

Example 15

Preparing Targeted Constructs Using a Microparticulate Linking Component and a Mixture of IMG's Biotinylate a mixture of IMGs from a relevant source (e.g., the multiple strain variants of a multivalent pneumococcal polysaccharide vaccine or the various proteins or peptides from a viral vaccine) using a suitable reactive biotin reagent (in the case of oligosaccharides use a biotinylation reagent with a hydrazide reactive terminus (EZ-link hydrazide biotin, Pierce), and in the case of peptidic preparations use one with a terminus containing either a succinimidyl group for reaction with amines, a maleimidyl group for reaction with sulfhydryls, or an amine terminus reactive with carboxyls in the presence of ethylenediamine carbodiimide (EDC)). Add such a mixture of biotinylated IMGs to a targeting conjugate consisting of StAv bound to a biotinylated Mab, a biotinylated targeting peptide, such that the StAvs have remaining unoccupied biotin-binding sites. These are produced by reacting a large molar excess of StAv with the biotinylated targeting component. The biotinylated IMG mixture can also be reacted with liposomes bearing surface StAv molecules bound to lipid-bound biotin (e.g., biotinylated phosphatidyl ethanolamine), with sufficient unoccupied biotin-binding sites remaining on the bound StAv molecules. Administer and analyze as in Example 2.

Example 16

Using Anti-Band 3 Mab for Targeting IMGs to Senescent RBCs

Approximately 1% of RBCs are senescent and destined for removal from the circulation by phagocytosis in the RES. Their clearance is mediated by pre-existing natural IgG Abs (Nabs). These Nabs have low affinity for band 3. They can only bind their target Ag on the RBC firmly if the band 3 molecules are clustered in the RBC membrane, through augmented avidity. Band 3 clustering occurs as a result of cumulative oxidative damage in the course of the life of the cells. Use a slightly higher affinity anti-band 3 Mab, sufficiently high to out-compete the Nabs, but not so high as to bind all RBCs. The Mab can be a humanized IgG, for targeting IMGs to senescent RBCs.

To develop a human anti-band 3 Mab, immunize a mouse with human band 3 protein or with human red blood cells (which contain a senescent subpopulation) and fuse the spleen cells with a myeloma fusion partner (e.g., SP2/0). Plate fused cells at 100,000 cells/well in hybridoma selection medium (HAT). After 3 weeks screen supernatants of wells with hybridoma clones by ELISA on wells coated with band 3 protein extracellular domain. Subclone hybridomas that react specifically with human band 3 until the cultures are monoclonal. The resulting murine Mab can be "humanized" by methods familiar to those skilled in the art (e.g., Recombinant Antibodies (1999), Breitling, F. and Dübel, S. (eds.), John Wiley & Sons). Alternately, human anti-band 3 Mabs can be produced by fusion of normal human donor B cells, among which are found the cells producing anti-band 3 Nabs. Enrich B cells (the CD19+ or CD20+ subpopulation) from the peripheral blood mononuclear fraction by immunomagnetic purification (StemCell Sciences). Fuse the B cells by electrofusion (CytoPulse) to a suitable fusion partner myeloma or heteromyeloma cell line (e.g., K6H6/A5 or A6 (ATCC) or SP2-IL6-TERT (Dessain S K, et al., 2004, J Immunol Methods 291:109-122. High efficiency creation of human monoclonal antibody-producing hybridomas.)) to form hybridomas. Plate fused cells at 20,000 cells/well in hybridoma selection medium (HAT). After 3 weeks screen supernatants of wells with hybridoma clones by ELISA on wells coated with band-3 protein extracellular domain. Subclone band 3-specific IgG hybridomas. Purify the antibodies and use them to prepare an immune conjugate as described in Example 1. Use biotinylated influenza M2e peptide as the IMG and couple to the Mab with a StAv bridge. Assay in mice according to the method in Example 2.

What is claimed is:

1. An immune conjugate comprising: (a) a ligand that binds specifically to a cell surface molecule on a circulating non-lymphoid cell of a mammal, wherein said molecule comprises glycophorin A, wherein the ligand is an antibody; and (b) an immunogen coupled to said ligand, wherein the immunogen comprises an M2e peptide, wherein said immune conjugate, when administered to an individual, induces or enhances an immune response against said immunogen.

2. The immune conjugate of claim 1, wherein the ligand is biotinylated, glycosylated, acetylated, alkylated, isoprenylated, lipoylated, or phosphorylated.

3. The immune conjugate of claim 1, wherein the cell-surface molecule is on a red blood cell.

4. The immune conjugate of claim 1, wherein the circulating non-lymphoid cell is a red blood cell.

5. The immune conjugate of claim 1, wherein the mammal is human.

6. The immune conjugate of claim 1, wherein the M2e peptide is SEQ ID NO: 1.

7. The immune conjugate of claim 1, wherein the immunogen is biotinylated, glycosylated, acetylated, alkylated, isoprenylated, lipoylated, or phosphorylated.

8. The immune conjugate of claim 1, wherein the immunogen is coupled to the ligand via a covalent bond.

9. The immune conjugate of claim 1, wherein the immunogen is coupled to the ligand via a peptide bond, wherein the immune conjugate is a fusion protein.

10. A nucleic acid sequence encoding the fusion protein of claim 9.

11. An expression vector comprising the nucleic acid sequence of claim 10.

12. A host-cell comprising the expression vector of claim 11.

13. The immune conjugate of claim 1, wherein the immunogen is coupled to the ligand via a non-covalent bond.

14. The immune conjugate of claim 13, wherein the non-covalent bond is a biotin-avidin linkage.

15. The immune conjugate of claim 1, wherein the immune conjugate comprises two or more of said ligands.

16. The immune conjugate of claim 1, wherein the immune conjugate comprises two or more of said immunogens.

17. A composition comprising the immune conjugate of claim 1 and an adjuvant.

18. A method of inducing or enhancing an immune response against influenza A in a mammalian subject, the method comprising administering a therapeutically effective amount of the immune conjugate of claim 1, wherein an immune response to influenza A is induced in the mammalian subject.

19. The method of treatment of claim 18, wherein the mammalian subject is identified as suffering from or being at risk for an influenza A infection.

20. An article of manufacture comprising a measured amount of the immune conjugate of claim 1 and one or more items selected from the group consisting of packaging material, a package insert comprising instructions for use, a sterile fluid, and a sterile container.

21. An immune conjugate comprising: (a) a ligand that binds specifically to a cell surface molecule on a circulating non-lymphoid cell of a mammal, wherein said molecule comprises glycophorin A, wherein the ligand is an antibody; and (b) an immunogen coupled to said ligand, wherein the immunogen comprises an M2e peptide.

22. The immune conjugate of claim 1, wherein the M2e peptide is SEQ ID NO: 3.

23. The immune conjugate of claim 1, wherein the M2e peptide is SEQ ID NO: 4.

* * * * *

SEQUENCE LISTING

```
<160> NUMBER OF SEQ ID NOS: 13

<210> SEQ ID NO 1
<211> LENGTH: 23
<212> TYPE: PRT
<213> ORGANISM: Influenza A virus

<400> SEQUENCE: 1

Ser Leu Leu Thr Glu Val Glu Thr Pro Ile Arg Asn Glu Trp Gly Cys
1               5                   10                  15

Arg Cys Asn Asp Ser Ser Asp
            20


<210> SEQ ID NO 2
<211> LENGTH: 27
<212> TYPE: PRT
<213> ORGANISM: Hepatitis B virus

<400> SEQUENCE: 2
```

Phe Gly Ala Asn Ser Asn Asn Pro Asp Trp Asp Phe Asn Pro Asn Lys
1 5 10 15

Asp His Trp Pro Glu Ala Asn Gln Val Gly Ala
20 25

<210> SEQ ID NO 3
<211> LENGTH: 23
<212> TYPE: PRT
<213> ORGANISM: Influenza A virus

<400> SEQUENCE: 3

Ser Leu Leu Thr Glu Val Glu Thr Leu Ile Arg Asn Glu Trp Gly Cys
1 5 10 15

Arg Cys Asn Asp Ser Ser Asp
20

<210> SEQ ID NO 4
<211> LENGTH: 23
<212> TYPE: PRT
<213> ORGANISM: Influenza A virus

<400> SEQUENCE: 4

Ser Leu Leu Thr Glu Val Glu Thr His Ile Arg Asn Glu Trp Gly Cys
1 5 10 15

Arg Cys Asn Asp Ser Ser Asp
20

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Ala Gly Leu Ile
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Pro Gly Gly Gly
1

<210> SEQ ID NO 7
<211> LENGTH: 11
<212> TYPE: PRT
<213> ORGANISM: Plasmodium falciparum

<400> SEQUENCE: 7

Leu Lys Ser His Met Asn Arg Glu Ser Asp Asp
1 5 10

<210> SEQ ID NO 8
<211> LENGTH: 6
<212> TYPE: PRT
<213> ORGANISM: Artificial Sequence
<220> FEATURE:

-continued

<223> OTHER INFORMATION: Description of Artificial Sequence: Synthetic
peptide

<400> SEQUENCE: 8

Gly Ala Gly Ala Gly Ala
1 5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Gly Gly Gly Val Val Val
1 5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Glu Glu Glu Arg Arg Arg
1 5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Asp Lys Asp Lys Asp Lys
1 5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Pro Pro Pro Ser Ser Ser
1 5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Tyr Gln Cys Met Trp
1 5